United States Patent
Kassiri Bidhendi et al.

(10) Patent No.: US 10,953,230 B2
(45) Date of Patent: Mar. 23, 2021

(54) NEUROSTIMULATOR AND METHOD FOR DELIVERING A STIMULATION IN RESPONSE TO A PREDICTED OR DETECTED NEUROPHYSIOLOGICAL CONDITION

(71) Applicant: THE GOVERNING COUNCIL OF THE UNIVERSITY OF TORONTO, Toronto (CA)

(72) Inventors: Hossein Kassiri Bidhendi, Toronto (CA); Nima Soltani, Toronto (CA); Roman Genov, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 27 days.

(21) Appl. No.: 16/312,467

(22) PCT Filed: Jul. 19, 2017

(86) PCT No.: PCT/CA2017/050867
§ 371 (c)(1),
(2) Date: Dec. 21, 2018

(87) PCT Pub. No.: WO2018/014127
PCT Pub. Date: Jan. 25, 2018

(65) Prior Publication Data
US 2019/0126047 A1 May 2, 2019

Related U.S. Application Data

(60) Provisional application No. 62/364,643, filed on Jul. 20, 2016.

(51) Int. Cl.
*A61N 1/36* (2006.01)
*A61N 1/04* (2006.01)
(Continued)

(52) U.S. Cl.
CPC ........ *A61N 1/36135* (2013.01); *A61B 5/0031* (2013.01); *A61B 5/0042* (2013.01);
(Continued)

(58) Field of Classification Search
CPC .. A61N 1/0456; A61N 1/0476; A61N 1/0529; A61N 1/0551; A61N 1/36;
(Continued)

(56) References Cited

U.S. PATENT DOCUMENTS

| | | |
|---|---|---|
| 6,597,954 B1 | 7/2003 | Pless et al. |
| 7,212,110 B1 | 5/2007 | Martin et al. |

(Continued)

FOREIGN PATENT DOCUMENTS

| | | |
|---|---|---|
| CN | 102157989 | 8/2011 |
| WO | 2008/109508 A2 | 9/2008 |
| WO | 2015092747 A2 | 6/2015 |

OTHER PUBLICATIONS

Supplementary Partial European Search Report for EU patent application No. 16852943.6, EPO, dated Apr. 11, 2019.
(Continued)

*Primary Examiner* — Christopher A Flory
(74) *Attorney, Agent, or Firm* — Bhole IP Law; Anil Bhole; Marc Lampert

(57) ABSTRACT

There is provided a neurostimulator and method for delivering to a subject a stimulation in response to a predicted or detected condition. The neurostimulator including: a power circuit for providing electrical power to the neurostimulator; a recording array having a plurality of electrodes for recording a plurality of neurophysiological signals corresponding to a plurality of sites of the subject; a signal processor configured to: determine a phase synchrony among the neurophysiological signals; and associate selected phase synchrony calculations with the prediction or detection of a
(Continued)

neurological or neurophysiological condition; and one or more stimulators for delivering to the subject a stimulation in response to the predicted or detected condition.

11 Claims, 25 Drawing Sheets

(51) Int. Cl.

| | | |
|---|---|---|
| *A61N 1/375* | (2006.01) | |
| *A61B 5/00* | (2006.01) | |
| *A61B 5/145* | (2006.01) | |
| *A61B 5/0496* | (2006.01) | |
| *A61N 1/05* | (2006.01) | |
| *A61B 5/0402* | (2006.01) | |
| *A61B 5/0476* | (2006.01) | |
| *A61N 1/378* | (2006.01) | |
| *G06N 20/00* | (2019.01) | |

(52) U.S. Cl.
CPC .......... *A61B 5/0402* (2013.01); *A61B 5/0476* (2013.01); *A61B 5/0496* (2013.01); *A61B 5/14532* (2013.01); *A61B 5/14546* (2013.01); *A61B 5/4094* (2013.01); *A61B 5/686* (2013.01); *A61B 5/7225* (2013.01); *A61B 5/7275* (2013.01); *A61B 5/7282* (2013.01); *A61N 1/0456* (2013.01); *A61N 1/0476* (2013.01); *A61N 1/0529* (2013.01); *A61N 1/0551* (2013.01); *A61N 1/36* (2013.01); *A61N 1/36031* (2017.08); *A61N 1/36034* (2017.08); *A61N 1/36057* (2013.01); *A61N 1/36139* (2013.01); *A61N 1/3756* (2013.01); *G06N 20/00* (2019.01); *A61N 1/3787* (2013.01); *A61N 1/37514* (2017.08)

(58) Field of Classification Search
CPC ............ A61N 1/36031; A61N 1/36034; A61N 1/36035; A61B 5/0031; A61B 5/0042; A61B 5/0402
See application file for complete search history.

(56) References Cited

U.S. PATENT DOCUMENTS

| | | | |
|---|---|---|---|
| 8,180,452 B2 | 5/2012 | Shaquer | |
| 9,030,239 B1 | 5/2015 | Dastgheib et al. | |
| 2002/0172069 A1 | 11/2002 | Thompson et al. | |
| 2004/0068199 A1 | 4/2004 | Echauz et al. | |
| 2005/0075282 A1* | 4/2005 | Coulter ................. | A61K 31/19 514/570 |
| 2005/0197590 A1* | 9/2005 | Osorio ................. | A61B 5/4094 600/544 |
| 2007/0050046 A1* | 3/2007 | Georgopoulos ..... | A61B 5/0476 623/24 |
| 2007/0067003 A1 | 3/2007 | Sanchez et al. | |
| 2007/0150024 A1 | 6/2007 | Leyde et al. | |
| 2007/0213786 A1 | 9/2007 | Sackellares et al. | |
| 2008/0039904 A1* | 2/2008 | Bulkes ................. | A61N 1/3622 607/62 |
| 2008/0176271 A1 | 7/2008 | Silver et al. | |
| 2009/0079607 A1* | 3/2009 | Denison ............... | A61B 5/7203 341/143 |
| 2010/0168603 A1* | 7/2010 | Himes ................. | A61B 5/4094 600/544 |
| 2010/0197524 A1 | 8/2010 | Janata et al. | |
| 2010/0274321 A1* | 10/2010 | Libbus ............... | A61N 1/36114 607/59 |
| 2011/0004268 A1* | 1/2011 | Tcheng .............. | A61N 1/36135 607/45 |
| 2011/0130797 A1 | 6/2011 | Talathi et al. | |
| 2011/0306847 A1 | 12/2011 | Lowry et al. | |
| 2012/0053449 A1* | 3/2012 | Moses ................. | A61B 5/4836 600/411 |
| 2012/0078071 A1 | 3/2012 | Bohm et al. | |
| 2012/0283800 A1 | 5/2012 | Perryman et al. | |
| 2013/0035745 A1* | 2/2013 | Ahmed .............. | A61N 1/36103 607/66 |
| 2013/0172774 A1 | 7/2013 | Crowder et al. | |
| 2013/0178731 A1* | 7/2013 | Bosl ................... | A61B 5/04012 600/409 |
| 2014/0012122 A1 | 1/2014 | Sadek et al. | |
| 2014/0081094 A1* | 3/2014 | Jordan ................. | A61B 5/725 600/301 |
| 2014/0213874 A1* | 7/2014 | Tong .................... | A61B 5/6803 600/383 |
| 2014/0257128 A1* | 9/2014 | Moxon ............... | A61B 5/7282 600/544 |
| 2014/0267163 A1* | 9/2014 | Hotelling ............. | G06F 3/0414 345/174 |
| 2014/0336948 A1* | 11/2014 | Qin ........................ | H03G 3/001 702/19 |
| 2014/0371515 A1* | 12/2014 | John ....................... | A61N 2/02 600/13 |
| 2014/0379046 A1* | 12/2014 | Tcheng .............. | A61N 1/36067 607/48 |
| 2014/0379620 A1* | 12/2014 | Sarrafzadeh ......... | A61B 5/0476 706/12 |
| 2015/0012111 A1* | 1/2015 | Contreras-Vidal ........................ | A61B 5/0476 623/25 |
| 2015/0206051 A1* | 7/2015 | McIntosh ............... | G06N 3/049 706/15 |
| 2016/0089540 A1* | 3/2016 | Bolea ........................ | A61F 5/56 607/42 |
| 2018/0269896 A1* | 9/2018 | Ouzounov ........... | H03M 3/496 |
| 2019/0059803 A1* | 2/2019 | Myers ................. | A61B 5/4094 |
| 2019/0143119 A1* | 5/2019 | Dzirasa ............... | A61N 1/0529 607/2 |
| 2019/0150774 A1* | 5/2019 | Brinkmann .......... | A61B 5/0006 |
| 2019/0314564 A1 | 10/2019 | Rudser et al. | |

OTHER PUBLICATIONS

Kassiri, Hossein et al.: Inductively-powered direct-coupled 64-channel chopper-stabilized epilepsy-responsive neurostimulator with digital offset cancellation and tri-band radio, 2013 Proceedings of the ESSCIRC (ESSCIRC), IEEE, Sep. 22, 2014, pp. 95-98.

Soltani, Nima et al., Cellular inductive powering system for weakly-linked resonant rodent implants, 2013 IEEE Biomedical Circuits and Systems Conference (Biocas), IEEE, Oct. 31, 2013, pp. 350-353.

European Search Opinion for EU patent application No. 16852943.6, EPO, dated Apr. 11, 2019.

Supplementary European Search Report for EU patent application No. 16806476.4, EPO, dated Jun. 18, 2019.

European Search Opinion for EU patent application No. 16806476.4, EPO, dated Jun. 18, 2019.

Panagiotis Kassanos et al: A CMOS magnitude/phase measurement chip for impedance spectroscopy, IEEE Sensors Journal, IEEE Service Center, New York, NY, US, vol. 13, No. 6, Jun. 1, 2013 (Jun. 1, 2013), pp. 2229-2236, XP011506442, ISSN: 1530-437X, DOI: 10.1109/JSEN.2013.2251628.

Office Action for U.S. Appl. No. 15/177,615; USPTO; dated Nov. 1, 2018.

Office Action for U.S. Appl. No. 15/177,615; USPTO; dated Aug. 9, 2018.

Schindler et al., "Increasing synchronization may promote seizure termination: Evidence from status epilepticus", Jun. 18, 2007, Clinical Neurophysiology, 118, 1955-1968.

Office Action for U.S. Appl. No. 15/177,615; USPTO; dated Dec. 31, 2018.

Advisory Action for U.S. Appl. No. 15/177,615; USPTO; dated Oct. 2, 2018.

Advisory Action for U.S. Appl. No. 15/177,615; USPTO; dated Jan. 30, 2019.

(56) References Cited

OTHER PUBLICATIONS

Supplementary Partial European Search Report for EU patent application No. 16806476.4, EPO, dated Feb. 14, 2019.
Panagiotis Kassanos et al: ACMOS Magnitude/Phase Measurement Chip for Impedance Spectroscopy, IEEE Sensors Journal, vol. 13, No. 6, Jun. 2013.
Office Action for U.S. Appl. No. 15/177,615; USPTO; dated Oct. 6, 2017.
Written Opinion of the International Searching Authority corresponding to PCT/CA2016/050655; Canadian Intellectual Property Office; dated Sep. 8, 2016.
International Search Report corresponding to PCT/CA2016/050655; Canadian Intellectual Property Office; dated Sep. 8, 2016.
International Search Report corresponding to PCT/CA2016/051169; Canadian Intellectual Property Office; dated Jan. 13, 2017.
Written Opinion of the International Searching Authority corresponding to PCT/CA2016/051169; Canadian Intellectual Property Office; dated Jan. 13, 2017.
International Search Report corresponding to PCT/2017/050867; Canadian Intellectual Property Office; dated Oct. 18, 2017.
Written Opinion of the International Searching Authority corresponding to PCT/CA2017/050867; Canadian Intellectual Property Office; dated Oct. 18, 2017.
"The 128-Channel Fully Differential Digital Integrated Neural Recording and Stimulation Interface" Shahrokhi et al [online], May 24, 2010 (May 24, 2010), [Retrieved on Oct. 12, 2017 (Oct. 12, 2017). Retrieved from: http://ieeexplore.ieee.org/document/5471738/authors?part=1.
"Design of an Optimal & Closed-Loop Neurostimulation System for treatment of Epilepsy" Gao, Richard, [online], Nov. 23, 2015 (Nov. 23, 2015], Retrieved on Oct. 12, 2017 (Oct. 12, 2017). Retrieved from: http:www,undergraduatelibrary.org/2014/medical-sciences/design-optimal-closed-loop-neuromodulation-system-treatment-epilepsy.
"Micropower CMOS Integrated Low-Noise Amplification, Filtering, and Digitization of Multimodal Neuroptentials" Mollazadeh et al. [online], Jan. 1, 2010 (Jan. 1, 2010). Retrieved Oct. 12, 2017 (Oct. 12, 2017). Retrieved from: https://www.ncbi.nlm.nih.gov/pmc/articles/PMC2747318/.
Weiss, S.R., et al., (1995) Quenching: Inhibition of Development and Expression of Amygdala Kindled Seizures With Low Frequency Stimulation. Neuroreport, 6:2171-2176.
Tergau, F., et al. (1999) Low-Frequency Repetitive Transcranial Magnetic Stimulation Improves Intractable Epilepsy. Lancet, 353:2209.
Osorio, I., Frei M.G. (2009) Seizure Abatement With Single DC Pulses: Is Phase Resetting at Play? International Journal of Neural Systems, 19:149-156.
Good, L.B. et al., (2009) Control of Synchronization of Brain Dynamics Leads to Control of Epileptic Seizures in Rodents. International Journal of Neural Systems, 19:173-196.
Lockman, J., Fisher, R.S. (2009) Therapeutic Brain Stimulation for Epilepsy. Neurologic Clinics 27:1031-1040.
Jiruska, P., et al. (2010) Effects of Direct Brain Stimulation Depend on Seizure Dynamics. Epilepsia 51:93-97.
Rashid, S. et al. (2012)Low Frequency Stimulation of Ventral Hippocampal Commissures Reduces Seizures in a Rat Model of Chronic Temporal Lobe Epilepsy. Epilepsia, 53:147-156.
Bagheri, A., et al. (2013) Massively-Parallel Neuromonitoring and Neurostimulation Rodent Headset With Nanotextured Flexible Microelectrodes. IEEE Transactions on Biomedical Circuits and Systems, 7:601-609.
Krook-Magnuson, E., et al. (2013) On-Demand Optogenetic Control of Spontaneous Seizures in Temporal Lobe Epilepsy. Nature Communications, 4:1376.
Koubeissi, M.Z. et al., (2013) Low-Frequency Electrical Stimulation of a Tiber Tract in Temporal Lobe Epilepsy. Annals of Neurology, 74:223-231.
Sun, F.T., Morrell, M.J. (2014) The RNS System: Responsive Cortical Stimulation for the Treatment of Refractory Partial Epilepsy. Expert Review of Medical Devices, 11:563-572.
Medeiros, D.D., Moraes M.F. (2014) Focus on Desynchronization Rather Than Excitability: A New Strategy for Intraencephalic Electrical Stimulation. Epilepsy Behav, 38C:32-36.
Colpan, M.E, et al., (2007) Proportional Feedback Stimulation for Seizure Control in Rats. Epilepsia, 48:1594-1603.
Abdelhalim, Karim, et al., "64-Channel UWB Wireless Neural Vector Analyzer SOC With a Neurostimulator", IEEE Journal of Solid-state circuits, IEEE, USA, vol. 48, No. 10, Oct. 1, 2013, p. 2494-2510.
Supplementary European Search Report for EU patent application No. 17830150.3, EPO, dated May 8, 2020.
European Search Opinion for EU patent application No. 17830150.3, EPO, dated May 8, 2020.
Office action for U.S. Appl. No. 15/580,823, United States Patent & Trademark Office, dated Sep. 3, 2020.
Office Action for U.S. Appl. No. 15/766,402, United States Patent & Trademark Office, dated Jul. 31, 2020.

\* cited by examiner (a)

(b)

NEUROSTIMULATOR AND METHOD FOR DELIVERING A STIMULATION IN RESPONSE TO A PREDICTED OR DETECTED NEUROPHYSIOLOGICAL CONDITION

TECHNICAL FIELD

The following relates generally to neurostimulators; and more particularly to a wearable or implantable neurostimulator and a method for monitoring, diagnosing and responding to neurophysiological disorders or conditions.

BACKGROUND

Micro-scale chips can be implanted or otherwise positioned in situ on a subject to measure target analytes. Integrating measurement functions of laboratory techniques into micro-scale implantable/wearable chips provides added convenience and accuracy of measurement. Excessive power draw from components of implantable/wearable micro-scale chips can limit utility given that power available to micro-scale chips is limited by either battery capacity or by the budget of a wireless power link. Further, excessive power consumption in such a chip may cause tissue damage to the surrounding area.

Several chips providing brain-neural interfaces have been reported in the literature; a handful of these are equipped with on-chip signal processing. However, the detection techniques of these chips are generally amplitude-based, resulting in late detection of neurophysiological events. For events such as epileptic seizures, a late detection makes it impossible to abort the seizures using responsive stimulation. Further, the published chips generally use OpAmp-based front-ends that can only tolerate up to a certain amplitude before being saturated. To combat this saturation, the published chips either use AC-coupled inputs which result in large recording channel area, or use DC-coupled front-ends with digitally-assisted feedback systems that can only reject up to ±50 mV, which is not sufficient in many cases.

The published neuro-stimulators are generally only capable of stimulating either a fixed pulse or at best a biphasic semi-programmable pulse train that is time-invariant and not subject-specific. These stimulators either have no programmability or require long stimulation parameter adjustment by a clinician for each new subject as well as frequent tuning over time for the same subject. Commercially-available neurostimulators are either open-loop (frequent periodic stimulation with no detection) or closed-loop with ineffective detection algorithms that result in very high false positive rate and inability to pre-emptively abort seizures due to late detection.

SUMMARY

In an aspect, there is provided a neurostimulator, the neurostimulator implantable or wearable on a subject, the neurostimulator comprising: a power circuit for providing electrical power to the neurostimulator; a recording array having a plurality of electrodes for recording a plurality of neurophysiological signals corresponding to a plurality of sites of the subject; a signal processor configured to: determine a phase synchrony among the neurophysiological signals; and associate selected phase synchrony calculations with the prediction or detection of a neurological or neurophysiological condition; and one or more stimulators for delivering to the subject a stimulation in response to the predicted or detected condition.

In a particular case, the responsive stimulation comprises any one or more of an electrical charge, electrical current, electrical voltage, optical signal, chemical agent and temperature controlling signal.

In another case, the power circuit comprises a wireless inductive link permitting a receiver coil to be located remotely from the neurostimulator.

In yet another case, the recording array records signals by electroencephalography, electrocardiography, electromyography, or a combination thereof.

In yet another case, the recording array is configured to record either current or voltage.

In yet another case, the neurostimulator further comprises a digitizer, and the recording array is linked to the digitizer for digitizing the neurophysiological signals.

In yet another case, the digitizer comprises an in-channel $\Delta\Sigma$ or $\Delta2\Sigma$ neural analog-to-digital converter.

In yet another case, the signal processor is a digital signal processor.

In yet another case, the recording array comprises sixty four channels.

In yet another case, the recorded signals are modulated by a 1-bit waveform, wherein the waveform is 1 when $\sin(\omega_o t)/\cos(\omega_o t) > 1$ and 0 when $\sin(\omega_o t)/\cos(\omega_o t) < 0$.

In yet another case, the stimulators comprise a waveform generator configured to generate an arbitrary current-mode waveform to be applied to a subset of the stimulators.

In yet another case, the arbitrary current-mode waveform is generated with a spatio-temporal profile determined specifically for the subject.

In yet another case, the determination of the spatio-temporal profile comprises a one-sided simultaneous perturbation stochastic approximation (SPSA), wherein for any particular stimulation the one-sided SPSA applies exactly one sampling of the phase synchrony to compute a gradient approximation.

In yet another case, the waveform generator provides an analog in-channel multiplier for the recording array.

In yet another case, the waveform generator provides the signal and its derivative for use in the calculation of phase synchrony.

In yet another case, the subset of the stimulators is selected based on one or more machine learning algorithms to provide optimal stimulation amplitude.

In another aspect, there is provided a method for neurostimulation comprising: applying a recording array to a subject; recording, by the recording array, a plurality of neurophysiological signals corresponding to plurality of sites of the subject; determining a phase synchrony among the neurophysiological signals; associating selected phase synchrony calculations with the prediction or detection of a neurological or neurophysiological condition; and delivering to the subject, by one or more stimulators, a stimulation in response to the predicted or detected condition.

In a particular case, the stimulators apply the stimulation comprising any one or more of an electrical charge, electrical current, electrical voltage, optical signal, chemical agent and temperature controlling signal.

In another case, the recording array records signals by electroencephalogram, electrocardiograms, electromyography, or a combination thereof.

In yet another case, the recording array is configured to record either current or voltage.

In yet another case, the method further comprising digitizing the neurophysiological signals prior to calculating the phase synchrony.

In yet another case, the digitizing comprises applying an in-channel $\Delta\Sigma$ or $\Delta2\Sigma$ neural analog-to-digital converter.

In yet another case, the recording array comprises sixty four channels.

In yet another case, the recorded signals are modulated by a 1-bit waveform, wherein the waveform is 1 when $\sin(\omega ot)/\cos(\omega ot)>1$ and 0 when $\sin(\omega ot)/\cos(\omega ot)<0$.

In yet another case, the stimulation comprises generating and applying an arbitrary current-mode waveform to a subset of the stimulators.

In yet another case, the arbitrary current-mode waveform is generated by a waveform generator using a spatio-temporal profile determined specifically for the subject.

In yet another case, the determination of the spatio-temporal profile comprises a one-sided simultaneous perturbation stochastic approximation (SPSA), wherein for any particular stimulation the one-sided SPSA applies exactly one sampling of the phase synchrony to compute a gradient approximation.

In yet another case, the waveform generator provides an analog in-channel multiplier for the recording array.

In yet another case, the waveform generator provides the signal and its derivative for use in the calculation of phase synchrony.

In yet another case, the subset of the stimulators is selected based on one or more machine learning algorithms to provide optimal stimulation amplitude.

These and other aspects are contemplated and described herein. It will be appreciated that the foregoing summary sets out representative aspects of neurostimulators and methods to assist skilled readers in understanding the following detailed description.

DESCRIPTION OF THE DRAWINGS

A greater understanding of the embodiments will be had with reference to the Figures, in which.

DETAILED DESCRIPTION

Figure 1:
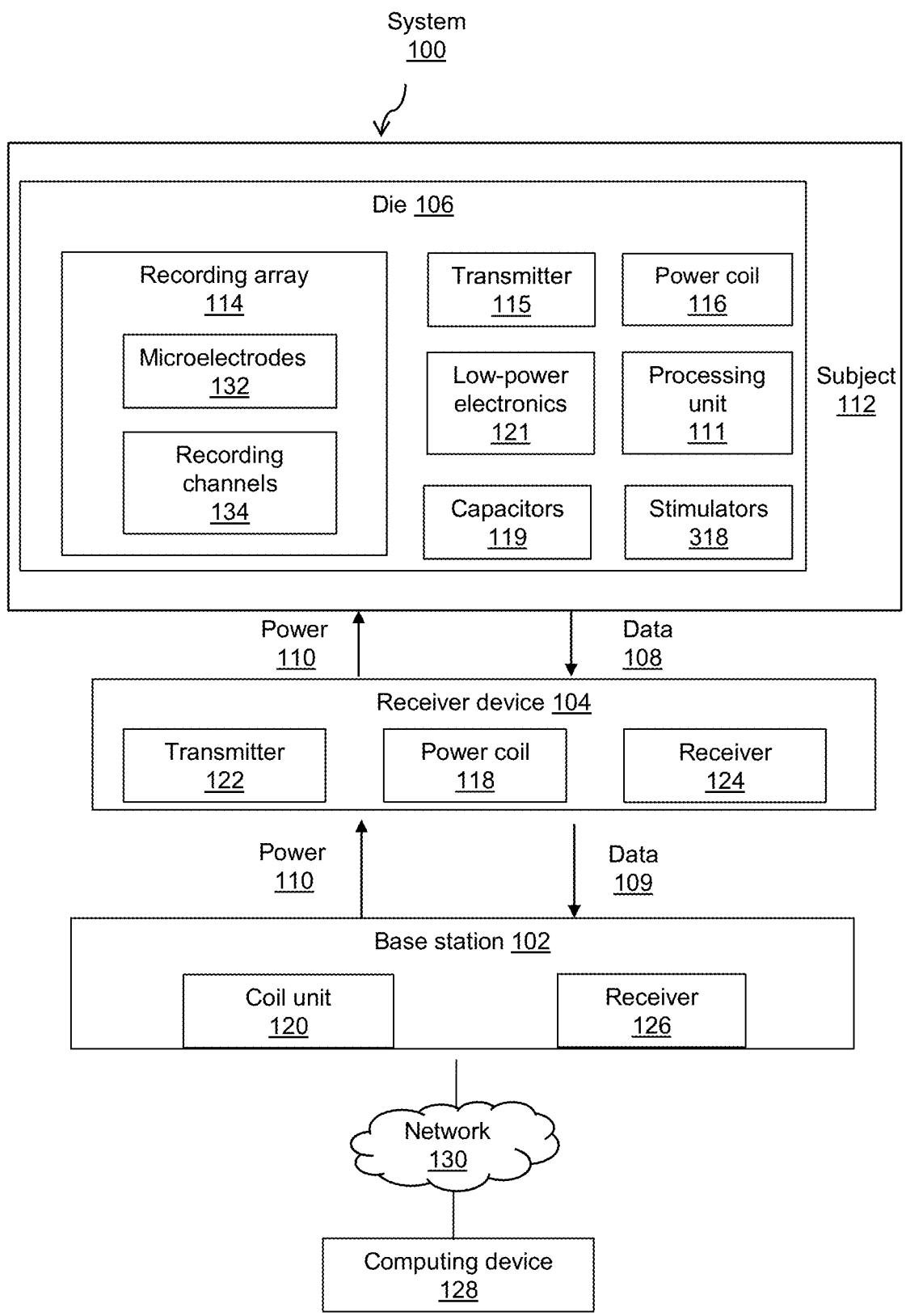
FIG. 1 shows a block diagram of a system for in situ monitoring, diagnostics and responsive stimulation of various neurophysiological disorders.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa;

similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Embodiments described herein generally provide a millimetre scale package-free complementary metal-oxide-semiconductor ("CMOS") chip (referred to below as "die") for the in situ (on-site) high-spatial resolution measurement of electrochemically detectable analytes (such as Na+, K+, Ca++ and glucose, for example), and for responsive stimulation by electrode stimulators to abort a neurophysiological event before its onset. Embodiments of the die comprise an electrode array and an associated recording channel array for measuring recording signals relating to target analytes.

More particularly, the embodiments provide a closed loop responsive neurostimulator device that is capable of recording both electrical voltages and currents, on-chip signal processing and arbitrary waveform electrical (current or voltage) and optical stimulation. The voltage recording is used for monitoring neurophysiological signals such as EMG, ECG and brain EEG and ECoG. The current recording capability enables applications such as Na+ and K+ ion concentration monitoring (which may be used for neurological event detection), impedance spectroscopy, and cyclic voltammetry. Signal processing is described wherein phase is used as one of the features for neurological event detection. Signal processing techniques may include machine learning analysis. Further, optimal patient-specific time-variant electrical stimulation may be implemented.

The die comprises recording channels providing a hardware implementation of synchrony-based neurological event detection (such as early epileptic seizure detection). The described switched-capacitor-based implementation prevents amplifier saturation from high input signal amplitudes or DC offset variations by recording rail-to-rail signal amplitude/DC-offset variations. This ensures the die is useful not only for neurological monitoring (e.g. electroencephalogram "EEG"), but also for other technologies that provide a measurable signal array, such as electromyography ("EMG"), electrocardiograms ("ECG"), etc.).

The die also provides stimulators for responsive stimulation requiring minimal tuning of stimulation parameters over time and from subject to subject. The die comprises a processing unit communicatively coupled to both the stimulators and to the recording channels, that may implement a machine-learning based technique for feature detection from recorded signals that auto-adjusts a stimulation profile to optimal values for each new subject over time.

An inductive power transfer system and a short-range communication circuit power and communicate with the die simultaneously. Due to circuits used in design of the front-end of the recording channels and a local signal processing unit, total power consumption fits within the inductive power transmission link budget.

The die may thus be fully-implantable, wireless and capable of early detection of neurophysiological events (such epileptic seizure). The die may further provide responsive subject-specific stimulation.

Further, embodiments of the recording channel of the die are described which may minimize size and power consumption by multiplying recording channel outputs by a 1-bit waveform ("1" when $\sin(\omega_o t)/\cos(\omega_o t) > 1$ and "0" when $\sin(\omega_o t)/\cos(\omega_o t) < 0$) utilizing a XOR gate, instead of high-resolution $\sin(\omega_o t)$ and $\cos(\omega_o t)$ waveforms. The single XOR gate replaces the many digital logic gates of conventional impedance spectroscopy ("IS") circuits.

Further, embodiments described herein provide a zero-hysteresis comparator circuit which may reduce or eliminate signal distortion. This circuit may reduce naturally occurring hysteresis in the comparator by isolating the output of the comparator from its input.

Referring now to FIG. 1, a block diagram of a system 100 for in situ monitoring, diagnostics, and responsive stimulation of various neurological or neurophysiological disorders or conditions is shown. The system 100 comprises a base station 102, an optional receiver device 104 and a die 106, the components and functionality of which will be described in more detail below. In use, the die 106 may be positioned in situ for measurement of target analytes of a subject 112.

The die 106 comprises a recording array 114 comprising associated recording channels 134 for recording signals relating to electrochemical reactions occurring at an electrode-tissue interface, such as interactions with chemically bonded analytes, and digitizing the signals for transmission. More particularly, die 106 may comprise microelectrodes 132. In some cases, along at least one of its surfaces a plurality of microelectrodes 132 are used for bonding chemically with targeted analytes when the die is positioned at a location of interest of a subject 112, in situ, and activated. The die further comprises a transmitter unit 115 for transmitting data relating to the recorded sensor signals, a power coil 116 for receiving energy (and possibly control signals and a clock) by magnetic induction from the receiver device 104 or base station 102, low-power electronics 121, and a bank of capacitors 119 for storing energy on the die to power the low-power electronics 121. The die may comprise a processing unit 111 for processing recorded signals locally at the die; and stimulators 318 (which may be any one or more of electrical/optical/chemical/temperature-based), triggered upon the prediction/detection of the onset of a target neurophysiological event from the recording signals.

The receiver device 104 comprises a transmitter 122, a receiver 124 and a power coil 118. The base station 102 comprises a receiver 126 and a power coil 120. The die 106, receiver 104 and base station 102 comprise other components as set out in more detail below with reference to particular embodiments.

In use, the die 106 transmits data comprising recorded signals (illustrated as block 108) to the receiving device 104, and receives power therefrom (illustrated as block 110). Similarly, the receiver device 104 transmits data received from the die to the base station 102 and receives power therefrom, as illustrated by blocks 109 and 110, respectively. The base station 102 may be communicatively linked over a wired or wireless network 130 with a computing device 128 for processing received data. Optionally, data may be processed locally at the base station 102 if the base station comprises hardware for processing the data, or at the die 106. Alternatively, the die 106 may be directly linked with the base station 102, and the communication of power and data may occur over a wired connection.

Figure 2:
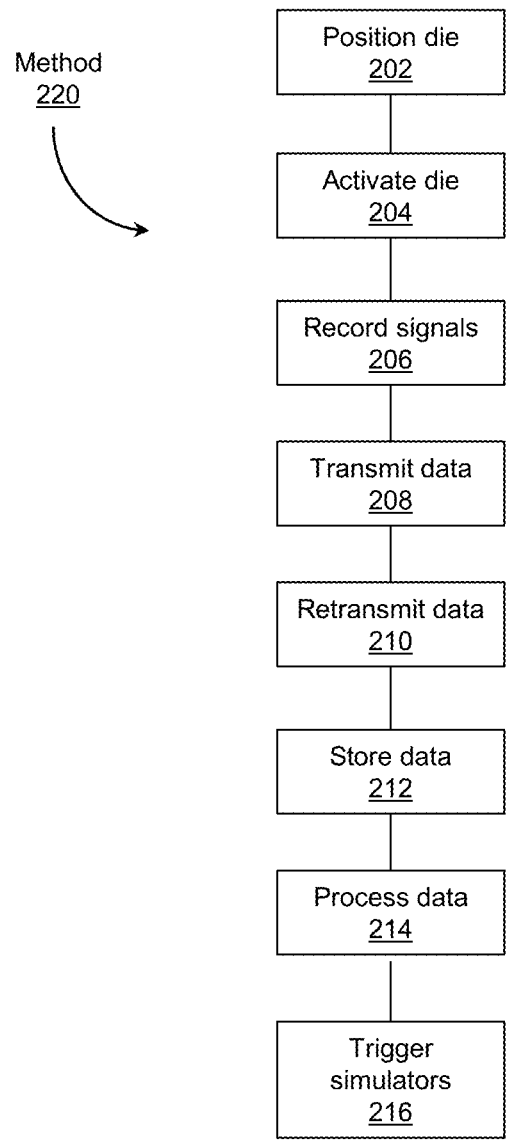
FIG. 2 shows flowchart for a method for in situ monitoring, diagnostics and responsive stimulation of various neurophysiological disorders.

Referring now to FIG. 2, a method 220 for in situ monitoring, diagnostics and responsive stimulation of various neurophysiological disorders is shown. According to the method 220 at block 202 the die 106 is positioned at a location of interest in or on a subject 112. This location might, for example, be adjacent to the subject's eye, brain, or other tissue for which analyte monitoring is desired. At block 204 the die is activated by the placement of a receiver device 104 or base station 102 nearby and the transmission of power to the die. At block 206 the die records signals responsive of electrochemical reactions occurring at the particular location making contact with the die's microelectrodes, such as signals indicative of the concentration of target analytes, such as ions, molecules, or microorganisms. More particularly, once the die is activated at block 204, the recording channels 134 of the recording module array 114 periodically record the electric charge accumulation on their corresponding microelectrode 132 and convert them to digital data. At block 208, the die may send out the recorded data using radio-frequency ("RF") waves via the transmitter unit 115 to the receiver 104 (or directly to the base station 102), positioned nearby, and preferably situated as close as possible to the die 106. At block 210, the data comprising the recorded signals may be buffered and re-transmitted to another RF receiver unit (referred to generally as base station 102) which could be farther away (e.g. meters or further) from the die 106 and the first receiver 104. At block 212, the data may be stored in memory at the receiver device 104 (or base station 102, if re-transmitted at block 210). At block 214, the data may be processed, either at the receiver device 104, base station 102 or at a communicatively linked computing device, depending on the configuration of the system. In some embodiments, the data may be processed locally at the die at a processing unit 111. At block 216, based on the processed data, prediction/detection of the onset of a target neurophysiological event may trigger electrical/optical/chemical/temperature-based stimulators 318.

Figure 3:
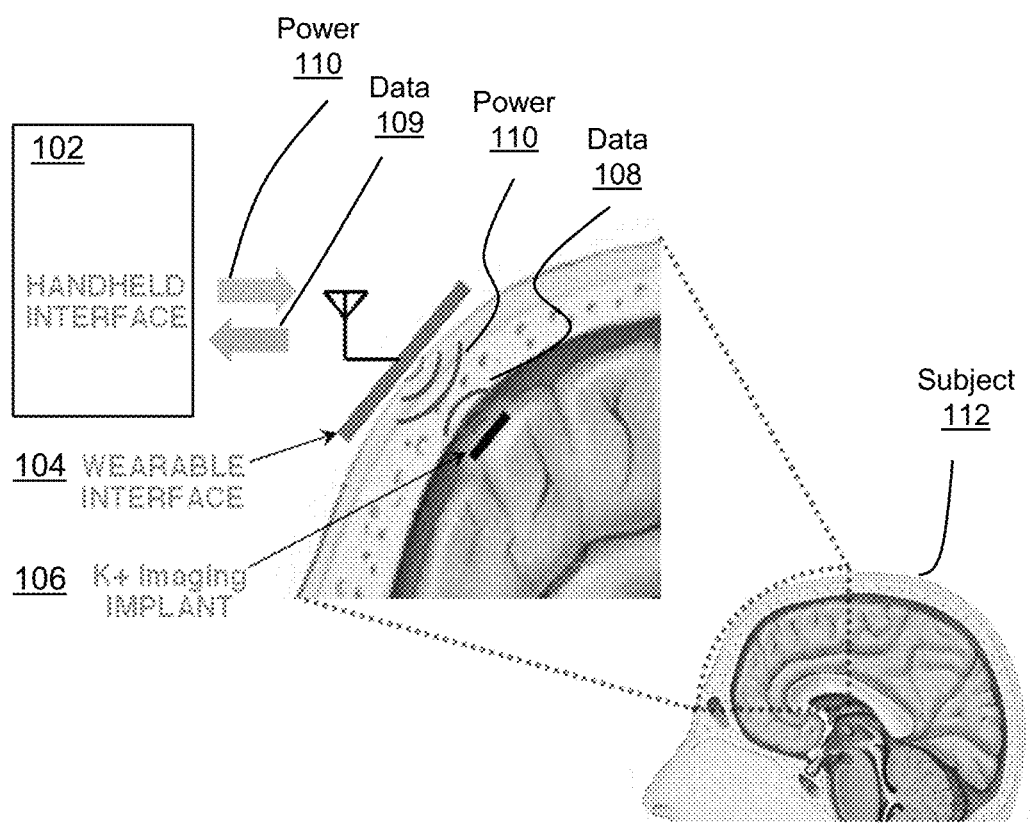
FIG. 3 shows application of the system of FIG. 1 for selective imaging of the concentrations of potassium (K+) ions over sodium (Na+) ions.

Referring now to FIG. 3, a particular application of the method 220 is shown, applying the in situ CMOS die 106 for selective imaging of concentrations of potassium (K+) ions over sodium (Na+) ions across the implanted region on the cortex of a free-moving subject 112. The die surface takes a 2-dimensional image of analyte concentration profile by simultaneously conducting impedance spectroscopy at all individual microelectrode sites in parallel and converting the resulting signals to digital words at the electrode location in the die. The digital bit stream created from all the microelectrodes data—i.e. impedance spectroscopy information from all individual on-chip microelectrodes in the die—is transmitted wirelessly outside the body to a receiver 104. Specifically, a miniature radio comprising a transmitter on the die communicates the recorded information to the receiving device 104. As illustrated, the receiving device 104 may be worn and may be placed on the surface of the subject's skin 112 as close as practically possible to the implanted die. The receiving device 104 may thus be constructed as a flexible patch. The wearable receiving device 104 then re-transmits this information by a more powerful radio to a base station 102 such as a handheld unit or a PC for analysis and display and/or permanent storage. The ionic concentrations provided from the imaging information may be useful for the diagnosis and possible abortion of seizure onsets in subjects with intractable epilepsy.

The neurological application provided in FIG. 3, and described in some instances below, is merely illustrative. It is contemplated that the die 106 could also be used for in situ measurement in other locations of interest and of other target analytes. For example, the die could be fabricated into a contact lens for measurement of glucose levels or other analytes along the surface of the eye. Description below of particular embodiments for neurological imaging are provided for illustration and are not intended to be limiting of contemplated applications.

Figure 4:
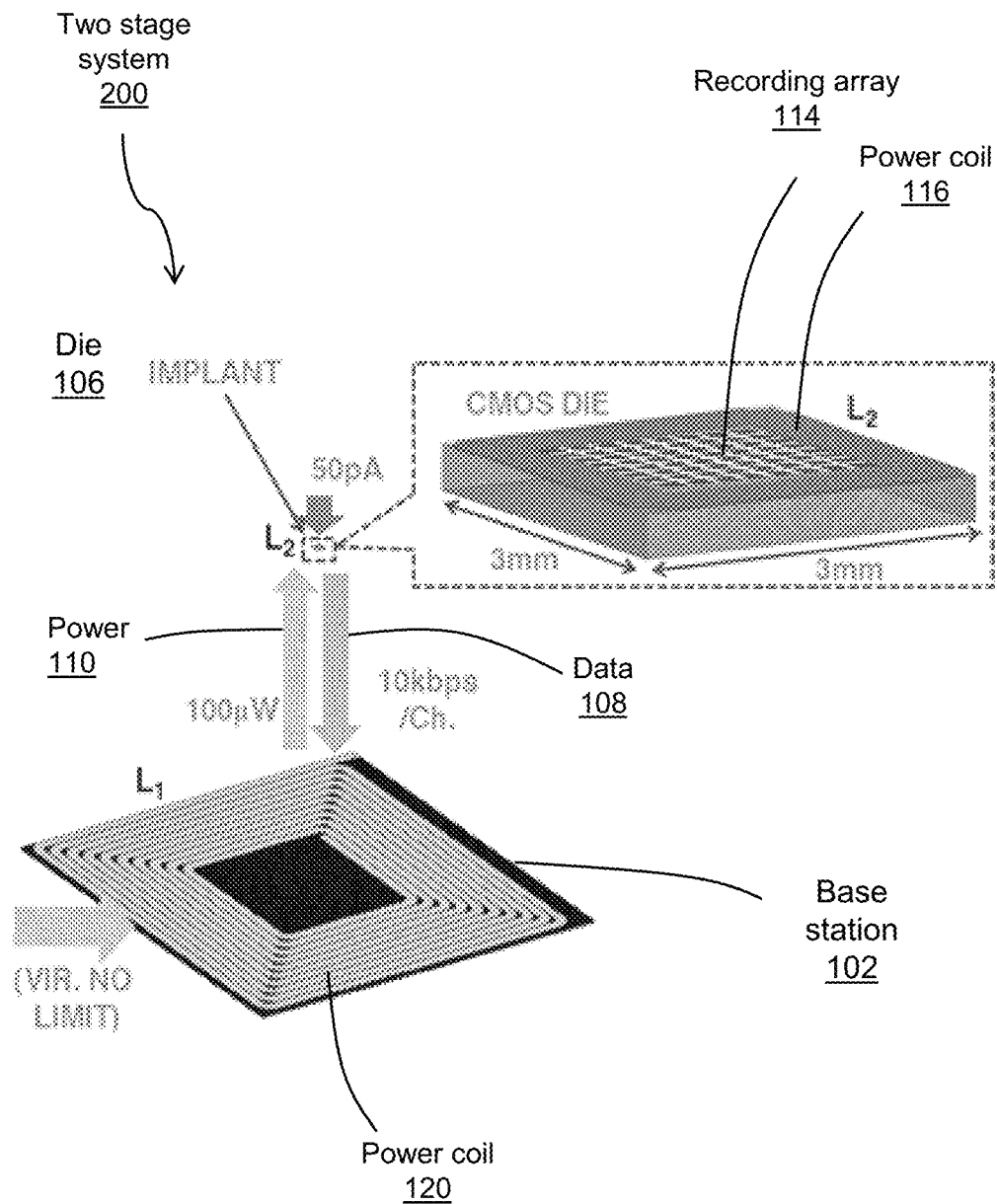
FIG. 4 shows a two-stage inductive powering system for in situ monitoring, diagnostics and responsive stimulation of various neurophysiological disorders.
Figure 5:
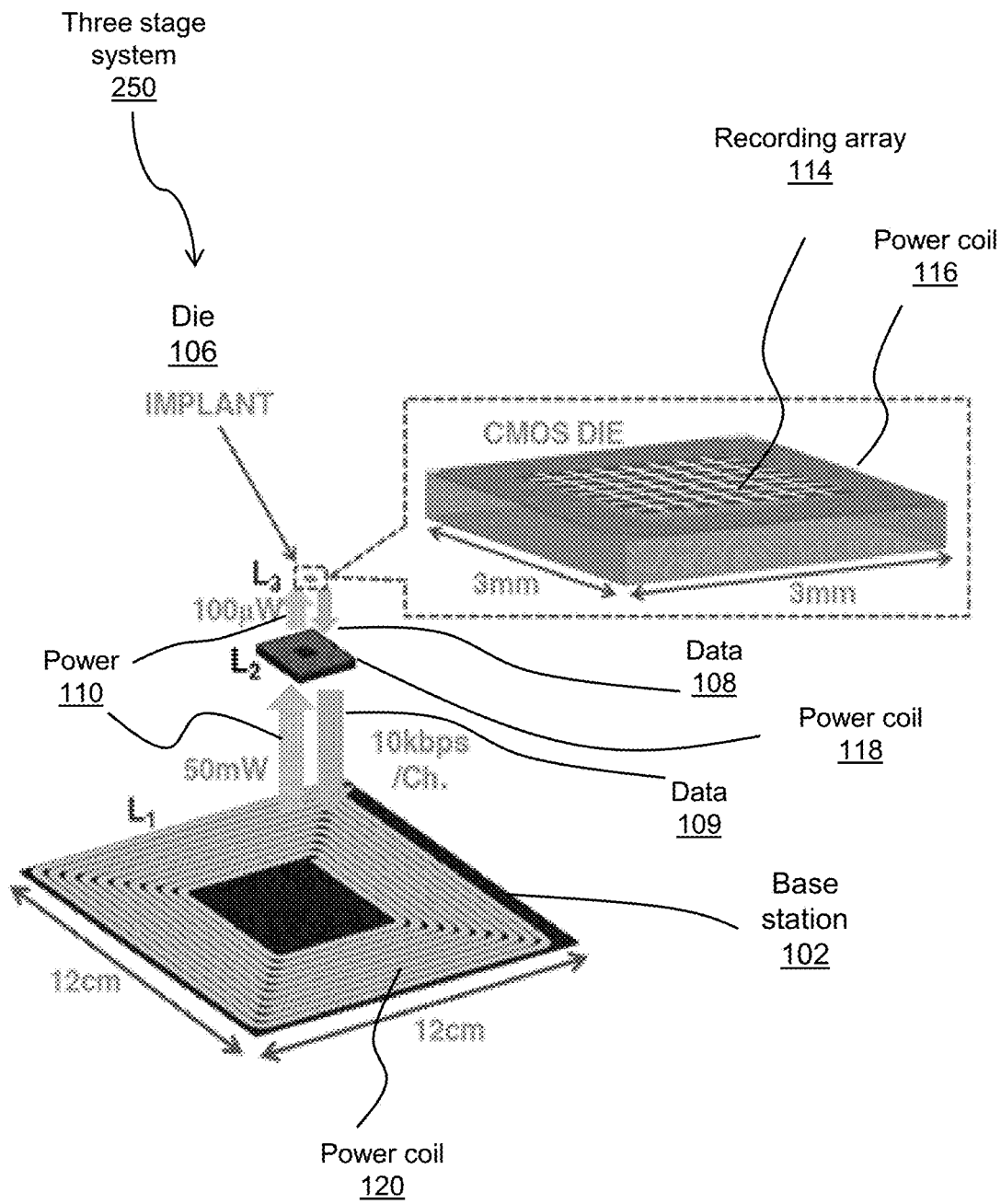
FIG. 5 shows a three-stage inductive powering system for in situ monitoring, diagnostics and responsive stimulation of various neurophysiological disorders.

Referring now to FIGS. 4 to 5, shown therein are further embodiments of systems 200, 250 for in situ monitoring, diagnostics and responsive stimulation of various neurophysiological disorders. The embodiments shown illustrate a two stage system 200 and a three stage system 250 used to wirelessly link the die 106 to the base station 102. Depending on the application, the die 106 can communicate directly with the base station 102 in a two stage system illustrated in FIG. 4, comprising stages L1 and L2. Alternately, according to a three stage system comprising stages L1, L2 and L3, a receiving device 104 may be provided at a second intermediary stage L2, to link with the base station 102, as shown in FIG. 5.

Describing now more particularly the components and functionality of the die, in an embodiment the die 106 comprises a recording array 114 comprising an array of electrodes 132, such as a 32×32 array, with a dedicated recording channel 134 fabricated underneath each electrode. The power coil 116 may be fabricated around the electrode array. Low-power electronics 121 comprising components for peripheral clock generation and data processing, as well as power management circuits may further be fabricated around the recording channel 134 array, underneath the energy harvesting power coil 116. The low-power electronics 121 may comprise circuit components, such as a delay-locked loop ("DLL"), an integrated digital-analog converter ("DAC"), a timing sequence generator, a 13-bit counter, a divide-by-8 frequency divider, a decoder, an amplitude-modulated demodulator ("AM Demodulator"), an analog to digital converter ("ADC"), a low-pass filter ("LPF"), a rectifier, a backscatter modulator and a multiplexer A storage capacitor bank may also be provided. With respect to the power management circuit of electronics 121, electric energy to power the die 106 microsystem may be generated by an integrated rectifier which can convert AC voltage induced in the energy harvesting power coil 116 into supply voltages, such as at 0.6V and 1.2V. Optionally, the 0.6V voltage may be used to power the all the digital circuits and the 1.2V supply can be used to power analog signal processing and the RF front-end data communication circuits.

Other components of the die are contemplated, as described in more detail below. For example, in some embodiments, the die includes a signal processing unit, power management circuit, wireless transmitters (UWB and FSK) and FIR Filters (such as 8 64-tap FIR Filters).

More particularly, the recording channels 134 are organized in the form of an array 114 in the center of the die underneath the electrodes 132. The area of the array may be surrounded on a top layer by the power coil 116. With regards to the electrodes 132, each column may comprise sixty four working electrodes and one reference electrode running alongside the column of working electrodes. During operation, the reference electrode may be driven by a periodic voltage signal (sinusoid, ramp, or sawtooth) while voltage of all the working electrodes may be held at a constant value (of approximately 300 mV to 500 mV). During a current-recording mode of operation, the current flowing into the working electrode as a result of its potential difference with the reference electrode may be recorded by a recording channel front-end operating essentially as a transimpedance amplifier. The output of the recording channel may be converted to digital words read by the array readout circuit after in-channel bandpass filtering.

Describing in more detail a mode of operation of a particular embodiment of the die 106, once the die is activated at block 204 of method 220, the channels 134 of the recording module array 114 periodically record the electric charge accumulation on their corresponding microelectrode 132 and convert them to digital data, such as 16-bit digital words which can be stored in 16 D-flip-flops fabricated inside each channel. After each conversion, the 16-bit content of all the channels may be extracted and serialized by a readout circuit (such as by a column decoder and row multiplexer). The column decoder may switch the content of the channels onto 16-bit bus lines running along the rows of the array. A multiplexer may sequentially read out the row buses once they are switched onto the D-flip-flops inside the individual channels. The multiplexer may produce two serial outputs corresponding to the less significant and the more significant bytes of channels' 134 data words. The serial outputs of the multiplexer may be fed into the on-chip radio transmitter which may send the data out to the base station 102 (in the two-stage setup), or the intermediate stage 104 (in the three-stage setup. This mode of operation thus multiplexes data for sending as an output. In another mode of operation, the data could also be sent to an on-chip signal processing unit (which could process the data for neurological event detection), and then the result of processing could be transmitted wirelessly to a receiver, which could be worn on the user's body or hand-held.

As described above, the energy to power the CMOS die 106 is delivered via magnetic induction from the receiving device 104 or base station 102 (illustrated as element 110). In the two stage system 200, the base station 102 generates an alternating magnetic field in power coil 120 which is induced into an integrated power coil 116 in the die. The magnetic energy is then converted to electric energy which is stored on a bank of capacitors 119 on the die to power components of the die, including low-power electronics 121. In the three-stage setup, the magnetic field created by the base station 102 is induced into a power coil 118 in the intermediate stage device 104 which then refocuses the magnetic field to better power the CMOS die. Operable geometries for the magnetic power coil in each stage, L1, L2, and L3, would be apparent to those of skill in the art.

Data transfer between the CMOS die 102 and the base station 102 or receiver 104 at element 108 may take place using either of two low-power radio transmission techniques: (a) ultra-wideband pulse radio ("UWB-IR") transmission, and (b) backscatter modulation techniques such as done in passive radio-frequency identification ("RFID") tags. As indicated by element 108 in FIG. 4, the CMOS die 106 communicates the data directly to the base station 102 in the two stage setup 200. A UWB-IR transmitter may be used in the two stage setup to accomplish this. In the three stage setup 250, the data may be backscattered to the intermediate stage at element 108 (as shown in FIG. 4). The data may then be relayed to the base station using a UWB-IR transmitter on the intermediate device 104 at element 109.

With respect to the clock generation of electronics 121, all the global clock, control and timing sequence signals may be generated from the alternating signal induced into the energy harvesting power coil 116 using the clock generation blocks. An illustrative 6.7 MHz signal of the power coil 116 may be converted to a preferred global clock, such as an 875 kHz global clock by a frequency divider, such as a divide-by-8 frequency divider. The global clock may then then used by 13-bit counter to generate all the 13-bit control signals for the MUX and the decoder in the readout circuit, as well as timing sequence signals used to run the individual digital potentiostat channels 134.

Referring now to FIGS. 6 to 17, particular embodiments of the die will now be described, providing a die capable of multi-channel recording of neurophysiological signals, on-chip feature extraction and responsive stimulation for the purpose of monitoring, diagnostics and/or responsive stimulation of various neurological or neurophysiological disorders. In such embodiments, feature extraction from monitored/recorded signals may be done in hardware on the die by measuring phase synchrony between signals from two or more recording sites; further, responsive stimulation may be performed by a stimulator by means of electrical charge, current, or electrical voltage, or an optical signal, or a combination thereof.

Figure 6:
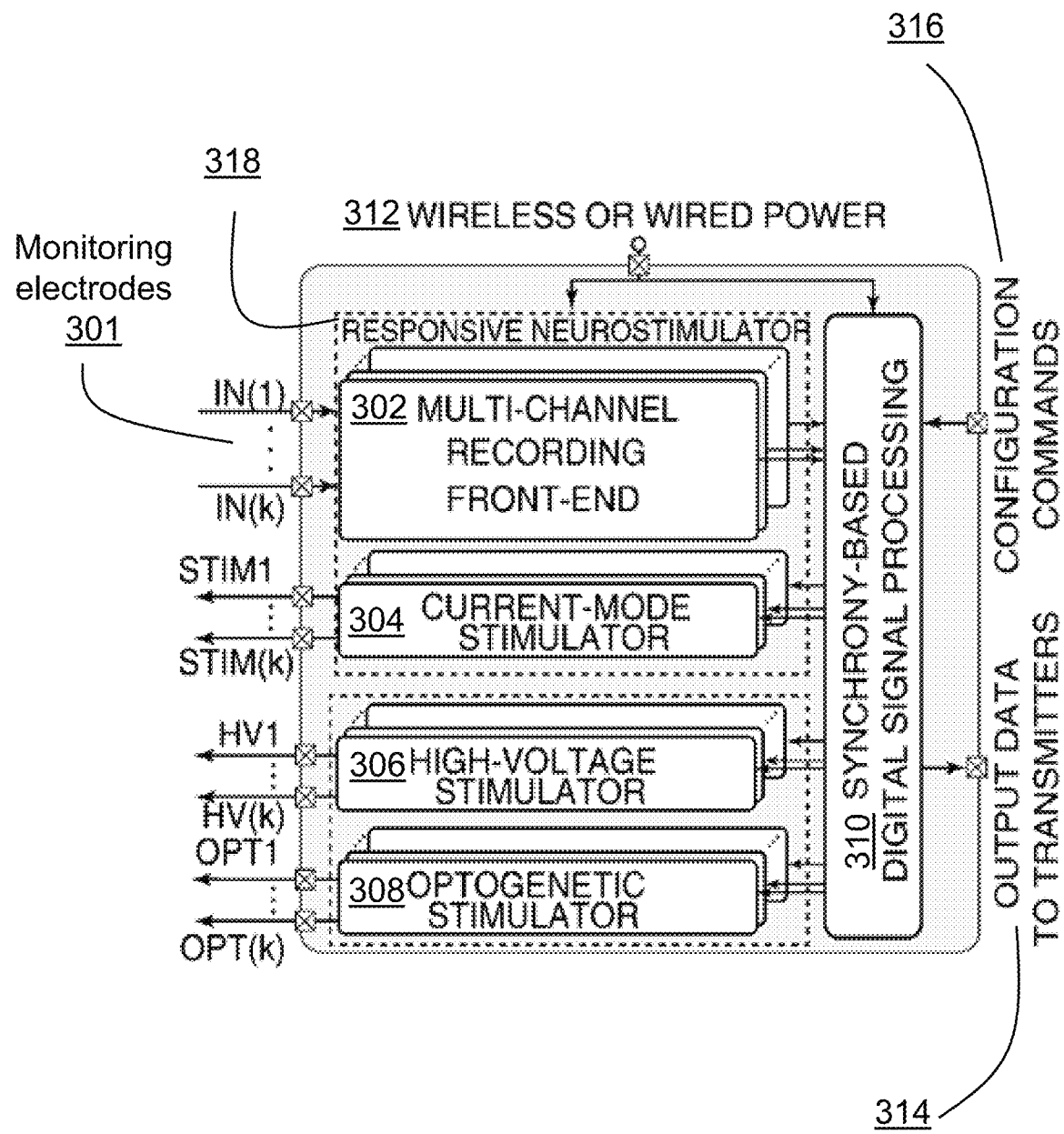
FIG. 6 shows a block diagram of an implantable/wearable die of a system for in situ monitoring, diagnostics and responsive stimulation of various neurophysiological disorders.

Referring now specifically to FIG. 6, shown therein is a block diagram of the die, providing local feature extraction and responsive stimulation. The die comprises: a recording array 114 having a multi-channel recording front-end 302 communicatively linked to monitoring electrodes 301 receiving signals—for which various embodiments will be described below with reference to FIGS. 6 to 12; a processing unit 111 having a synchrony-based digital signal processing unit 310; and a plurality of stimulators 318 coupled to the front-end 302 comprising at least one of a current-mode stimulator 304, a high-voltage stimulator 306, an optogenetic stimulator 308 or another type of stimulator.

Figure 7:
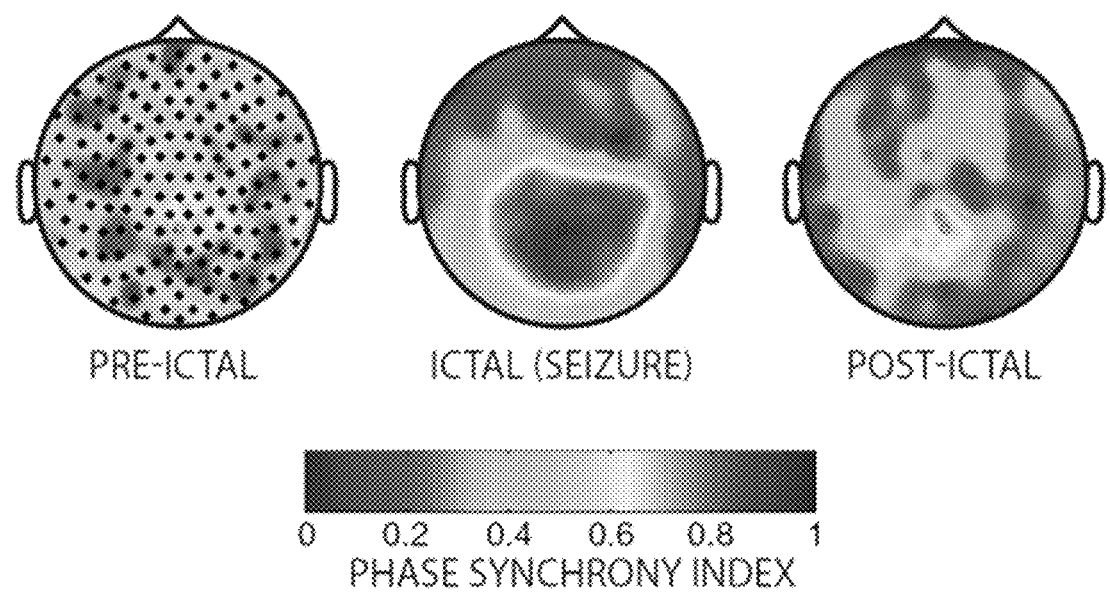
FIG. 7 shows possible inter-channel phase synchrony in a certain region of the brain (arrowed) and other regions (dots)

In use, the die receives recorded neurophysiological signals as electrical voltage or current at K different positions by the monitoring electrodes 301 coupled to the recording channels of the multi-channel recording front end, and provided as inputs 1 . . . K of the die. The die further receives wireless (inductive) or wired power 312 for supplying circuit blocks, such as from a power coil 116. The die may further receive control/configuration signals 316. The recorded neurophysiological signals may be subjected to amplification, filtering, and phase extraction in the recording front-end 302. The output of all channels may be sent to a central synchrony-based digital signal processing unit 310 where phase synchrony between two or more channels is calculated. For illustration, FIG. 7 shows possible inter-channel phase synchrony from a selected electrode (arrowed) and other electrodes (dots). The outcome of the phase-synchrony calculation may be used to predict/detect onset of a targeted neurophysiological event. Prediction/ detection of the onset of a target neurophysiological event may trigger an arbitrary subset of electrical/optical/chemical stimulators 318 back to the neurophysiological system. The recorded signals or/and the output of the processing unit may be transmitted to a computer base station using wired or wireless links as outputs 314 for processing and/or storage, such as through a UWB-IR transmitter of the die.

Figure 8:
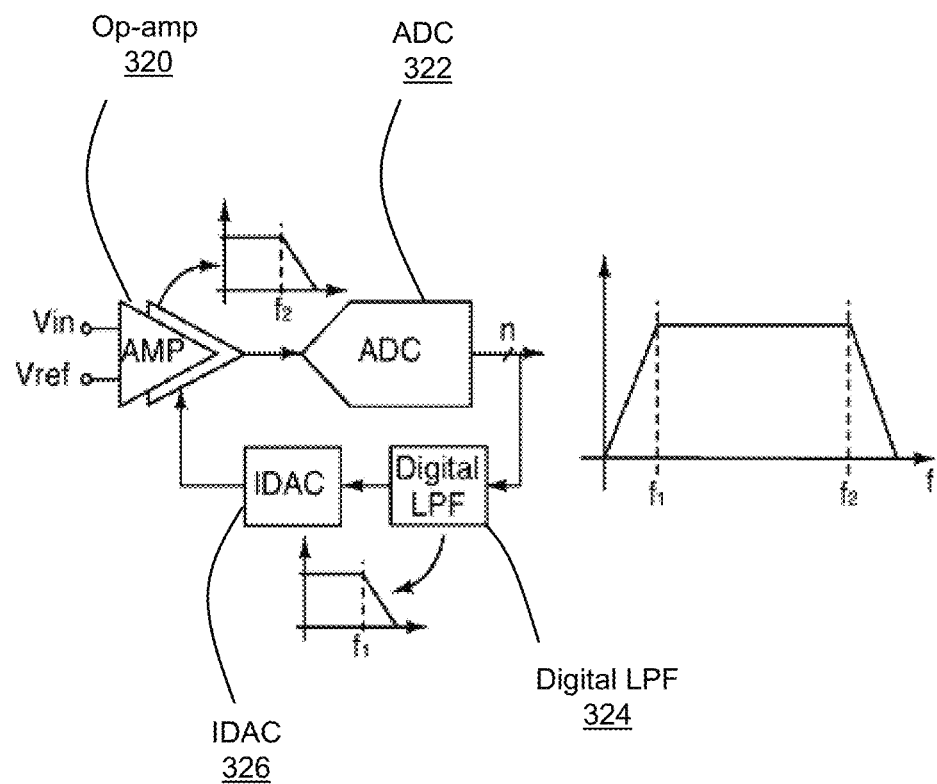
FIG. 8 shows a digitally-assisted analog front-end of a recording channel.

As described above, electrochemical reactions at the electrode-tissue interface may result in a significant DC input voltage level and DC drift—such as up to several hundred millivolts. In conventional front-end designs, to avoid front-end amplifier saturation, this DC offset may either be removed using AC coupling, or, to an extent, compensated for using a digitally assisted feedback loop in a DC-coupled design. According to architectures relying on AC coupling, to achieve both a low-frequency (<<1 Hz) high-pass pole and a high voltage gain, a coupled input capacitor must be large (>10 pF), and may be bulky, which may limit scalability with CMOS technology. This negatively affects the channel count and area of such designs, both of which are critical constraints in multi-channel neuromonitoring applications. An illustrative DC-coupled design is shown in the schematic of FIG. 8, comprising op-amp 320, ADC 322, digital LPF 324, and IDAC 326. In DC-coupled designs, the offset may thus be compensated for by including a digital feedback loop, eliminating the bulky input capacitor, however, only DC offset of up to ±50 mV may typically be removed and a long recovery time may be needed after a sharp transient. Additional bulky circuits are required to compensate for larger offsets and to calibrate for open-loop gain mismatch.

Though separate front-end 302, and stimulators 304, 306, 308 are illustrated in FIG. 6, the die may be configured to record from an electrode pair and stimulate using the same pair, such that electrodes enable dual functionality. In other embodiments the electrodes for recording and stimulation (and optionally each type of stimulation) are separate.

Figure 9:
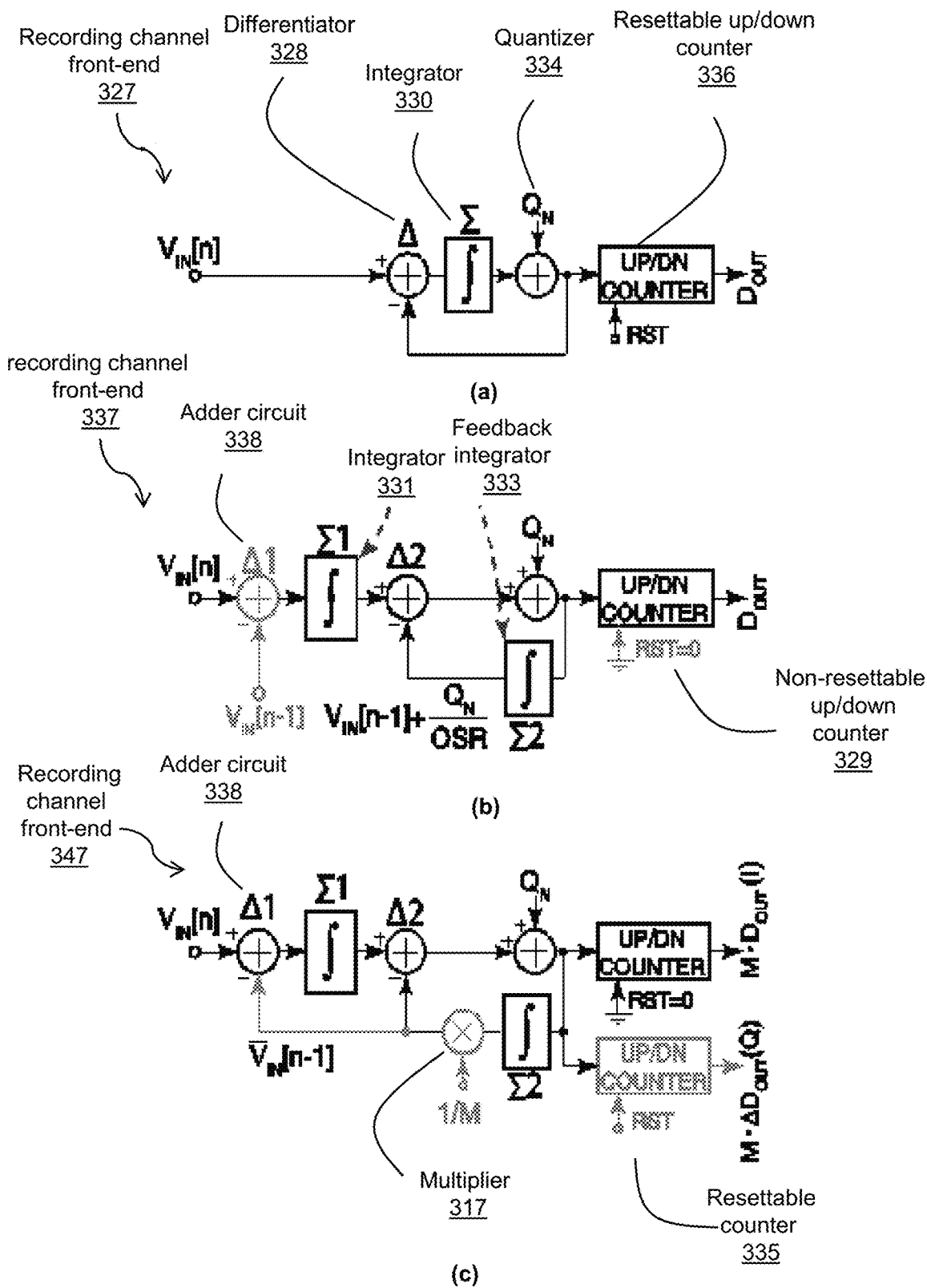
FIG. 9 shows simplified schematics of incremental design of a $\Delta^2\Sigma$-based front ends of recording channels of the neurostimulator die.
Figure 10:
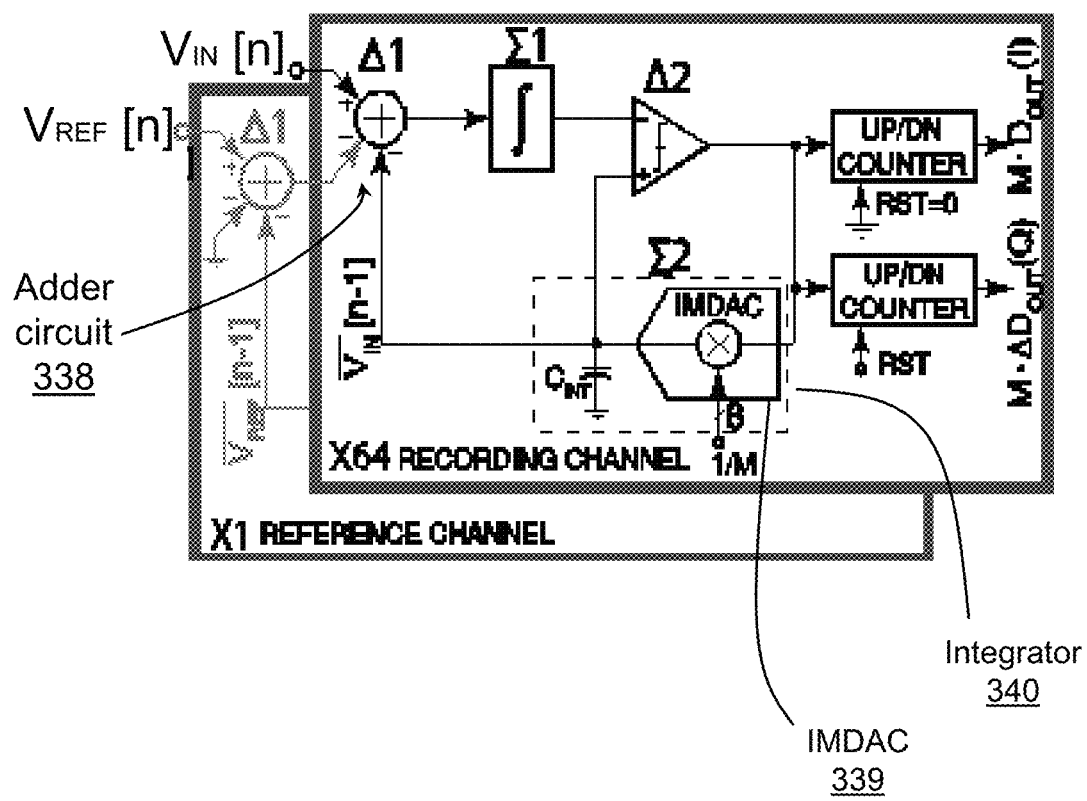
FIG. 10 further shows a simplified schematic of a $\Delta^2\Sigma$-based front end of recording channels of the die.

Referring now to FIGS. 9 and 10, specific embodiments of a multi-channel recording front-end 302 of the die will now be described. The described embodiments comprise an in-channel $\Delta\Sigma$ or $\Delta^2\Sigma$ neural ADC for each recording channel that records an intracranial electroencephalogram ("EEG") signal with an arbitrary rail-to-rail DC level, different for each of a plurality of recording channels including a reference channel. For simplicity and not by way of limitation, embodiments of the front end are described below having sixty four channels. The design of an embodiment of the multi-channel recording front-end 302 will be incrementally described with reference to simplified circuit schematics of FIGS. 9 and 10. The front-end 302 may be provided with other components of the die as a System on a Chip ("SoC").

FIG. 9(a) depicts a recording channel front-end 327 comprising a conventional first-order $\Delta\Sigma$ modulated ADC. The front-end 327 comprises a differentiator 328, an integrator 330, a quantizer 334 and a resettable up/down counter 336. [Such a circuit typically requires a small (~1 pF) input-sampling capacitor, and, for a high oversampling ratio ("OSR"), yields low input-referred thermal noise, but saturates for large input DC offsets.

In FIG. 9(b), a recording channel front-end 337 is shown where the integrator 330 is split into two integrators 331, 333 that are placed earlier in the signals paths. Saturation is eliminated by having consecutive samples, $V_{IN}[n]$ and $V_{IN}[n-1]$, being subtracted at an added differentiator 338 and their quantized difference integrated by a non-resettable up/down counter 329. FIG. 9(b) also shows that the previous sample plus the ADC quantization noise $(V_{IN})[n-1]$ is reconstructed at the output of the feedback integrator $\Sigma 2$ (shown as element 333) since the input of $\Sigma 2$ is equivalent to the signal derivative.

In FIG. 9(c), a recording channel front-end 347 is shown, where the signal from block 333 is connected to the subtracting input of $\Delta 1$ (element 338), to form a $\Delta^2\Sigma$ modulator. The derivative of the output is also computed by adding a resettable counter 335. This design results in two quadrature outputs, I and Q, with a 90° phase difference enabling subsequent phase computation on a signal tone. The tone selection within I and Q is implemented by a transposed mixed-signal finite impulse response ("FIR") filter 364, as described below, which requires signal scaling by a factor M and is implemented within the $\Delta^2\Sigma$ ADC by a multiplier 317 multiplying the feedback integrator ($\Sigma 2$) gain by a coefficient 1/M. This configuration minimizes amplitude and frequency constraints on the input, as larger signal amplitudes or higher frequencies that have sharper instantaneous slope only require the feedback loop to be faster to compensate for the difference between the two consecutive samples. This can be done either by increasing the clock frequency at the cost of higher dynamic power, or by multiplying the feedback integrator ($\Sigma 2$) gain by a coefficient greater than one compounded with the FIR coefficient 1/M.

FIG. 10 shows the differential implementation of FIG. 9(c) for an array comprising n differential recording channels providing the front end 302 (shown specifically for n=64). At adder circuit 338, the input signal derivative is additionally subtracted by the respective reference signal derivative, which eliminates the effect of common-mode ("CM") signal. An 8-bit current-output multiplying DAC (IMDAC) 339 and an integrating capacitor form the multiplying integrator 340.

The circuit schematic of multi-channel recording front-end 302 of FIG. 10 is shown more particularly in FIG. 11(a), providing $\Delta^2\Sigma$-based recording channels with outputs Q 394 and I 395. Circuit blocks provide input DC offset removal, Common Mode ("CM") noise removal and 1/f noise removal. A parasitic-insensitive differential integrator circuit performs both $\Delta 1$ and $\Sigma 1$ in one clock cycle (see 391, 392, 393 and amp 354). During a first portion of a clock cycle $\phi 1$ shown in FIG. 11(b), $C_{OFF}$ 356 samples the amplifier 354 input offset and 1/f noise, and keeps the common terminal of C1 and C1' at $V_{CM}$ during $\phi 2$ (a non-overlapping clock with respect to $\phi 1$). During $\phi 1$, C1 and C1' are charged to $V_{IN}[n]-V_{CM}$ and $V_{REF}[n-1]$-VCM, respectively. During $\phi 2$, one common terminal of C1 and C1' remains at the same voltage ($V_{CM}$) but the other terminal changes to $\overline{V_{IN}}[n-1]$ and $\overline{V_{REF}}[n]$, respectively. As a result the lower branch pushes a charge equal to C1*($V_{IN}[n]-\overline{V_{IN}}[n-1]$) and the upper branch pushes a charge equal to C1'*($\overline{V_{REF}}[n-1]$-VREF[n]). The charges are added and integrated on C2 thus implementing subtraction of the two derivatives and integration $\Sigma 1$. The two-stage 10T amplifier 354 is duty-cycled 5-50% for 0.5-5 kHz bandwidth respectively. One-bit quantization may be performed by a low-power 7T dynamic comparator 355. The illustrated IMDAC 352 comprises two segments of 4-bit binary-weighted programmable push/pull current sources. The segments are biased by two currents different by a factor of 16 for a total of 8 bits of resolution. On/off programmability of the current sources by an 8-bit word 1/M effectively implements compact analog-digital multiplication.

Figure 12:
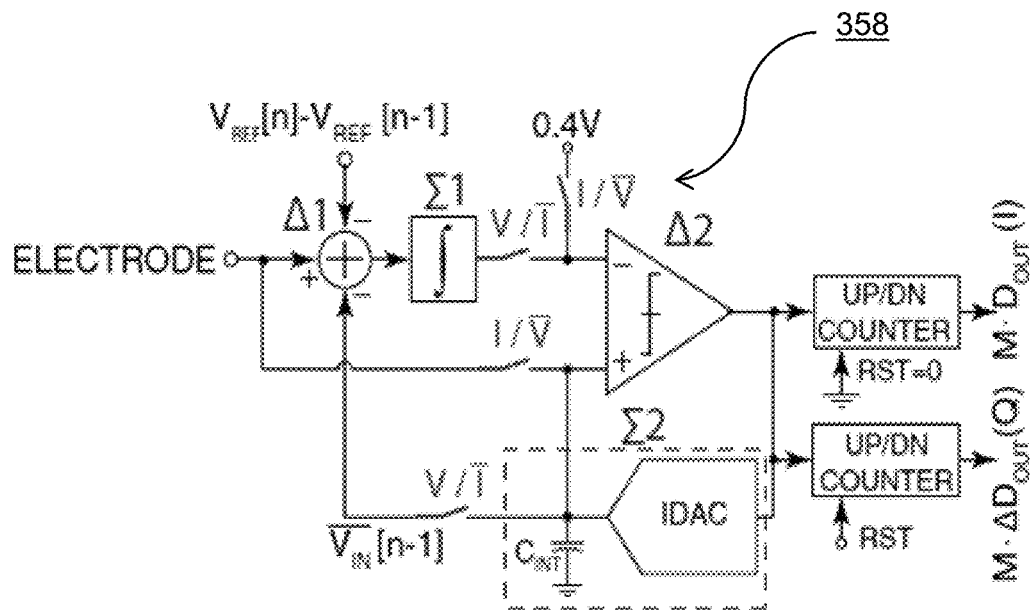
FIG. 12 shows a circuit of the front end of recording channels of the die for achieving a dual mode operation wherein the front-end is configured to record both electrical current and voltage.
Figure 12:
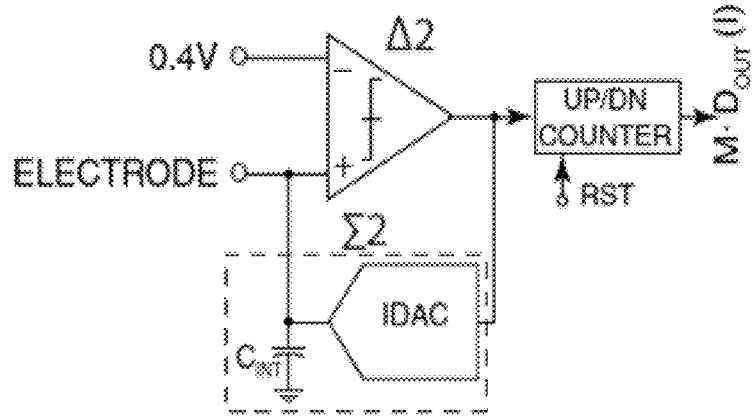

Referring now to FIGS. 12(a) and 12(b), shown therein is an architecture of the multi-channel recording front-end 302 for achieving a dual mode operation by recording both electrical current and voltage. The dual mode operation, together with voltage/current stimulation (described below) enables additional applications and capabilities to the die including impedance spectroscopy and motion artifact detection and removal. As shown in FIG. 12, the architecture can be reconfigured to current-recording mode simply by switching off the input voltage-integrator (as shown at block 358 of FIG. 12(a)) and using the reference node capacitance as the input current integrator (as shown in FIG. 12(b)).

As described above, the signals recorded by the recording channels may be processed by a processing unit of the die according to a phase-synchrony calculation. The prediction/detection of the onset of a target neurophysiological event may trigger an arbitrary subset of electrical/optical/chemical/temperature-based stimulators 318. Embodiments of the stimulators 318 and processing unit will now be described.

Figure 13:
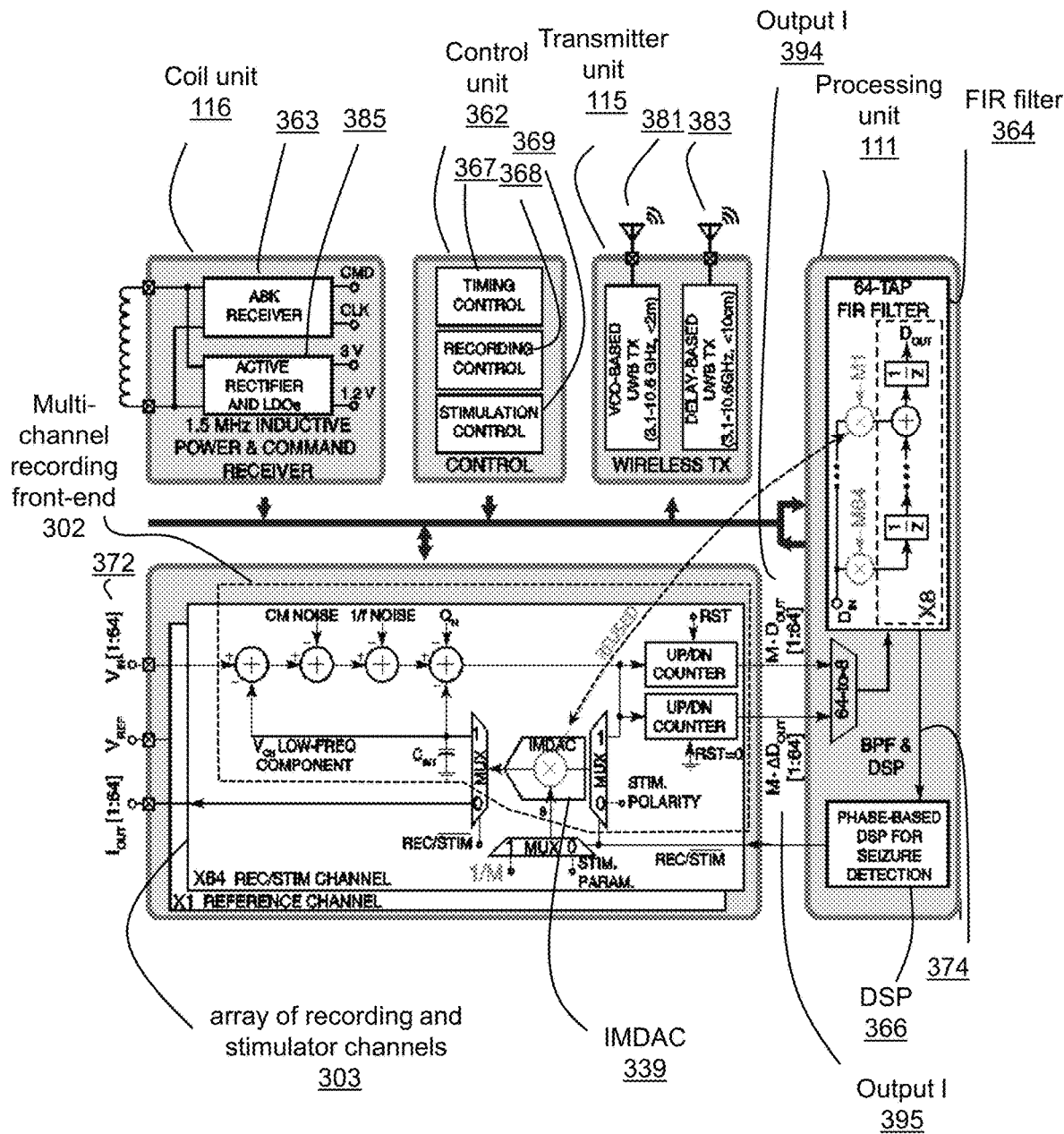
FIG. 13 shows a block diagram of the die comprising combined recording and stimulator channels.

Referring now to FIG. 13, shown therein is a block diagram of the die comprising a combined array of recording and stimulator channels 303, and associated peripheral blocks. The illustrated die provides sixty-four closed-loop arbitrary-waveform stimulators 318, each coupled to a recording channel of the multi-channel recording front end 302. The illustrated embodiment thus provides another embodiment providing the functionality of the recording front-end. The combined recording and stimulator channels 303 are coupled to peripheral blocks including a processing unit 111 comprising a low-power phased-based Digital Signal Processor ("DSP") 366 and a compact mixed-signal FIR filter 364 (described briefly above). The channels 303 are further coupled: to a transmitter unit 115 shown comprising a low-power delay-based short-range UWB transmitter 383 and a VCO-based long-range UWB transmitter 381; a power coil 116 for receiving command signals and power by induction, optionally comprising an ASK receiver 363, and an Active Rectifier and Low-drop out regulators ("LDO") 385; and a control unit 362 comprising a timing control unit 367, a recording control unit 368, and a stimulation control unit 369. The illustrated block diagram architecture of the stimulator unit may provide a VLSI architecture for fabrication of the die as a SoC. Further, as above, the illustration of a die comprising sixty four channels is merely illustrative.

The transmitter unit 115 may be operable to transcutaneously transmit recorded signals, such as EEG/ECoG data and status signals, received from the multi-channel front end 302. The transmitters may be used to communicate data to on-skin wearable receivers 104 (at a distance of less than 10 cm) and an indoor stationary receiver 102 (at a distance of perhaps less than 2 m), respectively. Power may be transmitted through power coil 116 through a multi-coil cellular inductive link, optionally at 1.5 MHz frequency. The power coil 116 may receive 30 mW maximum power for a 15 cm transmission distance with power efficiency of approximately 40 percent. ASK-demodulating command receiver 363 may use the inductive link of the power coil 116 to recover transmitted commands and the clock. Generally, the control unit 362 may receive control/clock signals (optionally from the ASK-demodulating command receiver 363) and may comprise logic to control operation of the die's components as described herein.

In use, in a detection mode of the die, each input signal received from recording electrodes at element 372, is fed to a recording channel of the multi-channel recording front-end 302, and to individual FIR filters 364 with coefficients M. All channels may be clocked X64 faster than the effective input sampling rate in order to implement the 64 IMDAC-enabled multiplications as needed in the 64-tap FIR tone-filter. The FIR filter tone outputs are fed (see element 374) to an on-chip DSP 366 that calculates the phase synchrony among channels to detect epileptic seizures.

If a prediction or detection is made at the DSP, a stimulation mode is triggered according to a spatio-temporal stimulation profile, which may vary stimulation temporally, and spatially (i.e. activating different electrodes). According to an illustrative stimulation profile, an arbitrary-waveform current-mode stimulation is applied to a subset of the electrodes with a spatio-temporal profile specifically chosen for a given subject In each channel the IMDAC 339 utilized in the neural recording $\Delta^2\Sigma$ ADC may be reused for stimulation (at a different programmable bias point) in a time-multiplexed fashion (see element 377). Thus arbitrary-waveform stimulation enabled by analog-digital multiplication is performed at almost no extra component area cost.

There is a lack of intelligent stimulation protocols for aborting seizures. One existing approach is constant-frequency and constant-amplitude bi-phasic stimulation in response to a binary signal indicating whether a seizure is present. While this type of non-adaptive stimulation demonstrates efficacy, the parameters often need fine tuning for patient-specific treatment by the clinician, on top of the fact that the parameters may change throughout a patient's long-term treatment period.

Another existing approach is a simple adaptive method which varies the frequency, amplitude, or length of the bi-phasic periodic stimulation, in response to the frequency or power of the neural synchrony present, in attempting to alter the phase of the subcomponents. This, and some other similar methods are adaptive but non-optimal, as they respond to state evaluations of the system in real-time in a predetermined way, i.e. the controller has a varying response but constant input-output relationship. Basically, the same system requires different responses even when the state variables are of the same value at a given instant in time, as is when two different system trajectories intersect.

An adaptive approach that tracks the actual system is finite difference stochastic approximation (FDSA). In essence, FDSA estimates the local gradient by approximating the partial derivative in every dimension:

$$\frac{\partial F}{\partial xi} = \frac{F(xi + \Delta) - F(xi - \Delta)}{2\Delta},$$

where $\Delta$ is an incremental change in xi. This provides an accurate estimate of the gradient locally, if $\Delta$ is small enough. If the system is nonstationary, FDSA is believed to guarantee that knowledge of which direction to take at any given time. However, a problem arises when the data dimension is very large, as it requires two samplings for every dimension. Not only is this a computational challenge, if the system state changes during sampling or due to sampling, then the gradient approximation may be unreliable. Therefore, it is ideal to sample as few times and as quickly as possible.

Simultaneous Perturbation Stochastic Approximation (SPSA) is another method that allows a decrease in the amount of sampling needed to compute a gradient approximation. SPSA simultaneously makes small perturbations along every dimension, forward and backward, in an organized way, such that only two samplings are required for every iteration. In the limit, SPSA is believed to converge to the optimal solution as FDSA does, but at a much faster rate in practice, especially in systems with high dimensionality.

The present system implements a discrete and one-sided version of the SPSA method, which will be referred to as D1-SPSA. D1-SPSA makes fast approximations of the cost function manifold in real-time, and aims to traverse towards a local minimum. The discrete version is used in conjunction with discrete-sized step changes in the stimulation parameters: frequency, amplitude, and phase. A key distinction of the one-sided algorithm used here is that, instead of using two samplings of the system to compute the gradient approximation, it uses one. Essentially, the controller perturbs the system stochastically and measures the performance of that stimulation: if the cost function is decreasing, we maintain the current perturbations or move even further along the previous direction; otherwise, stochastically change the parameters for the next cycle. A key reason for this choice is due to the fast moving nature of the system, even without controller stimulation.

Figure 14:
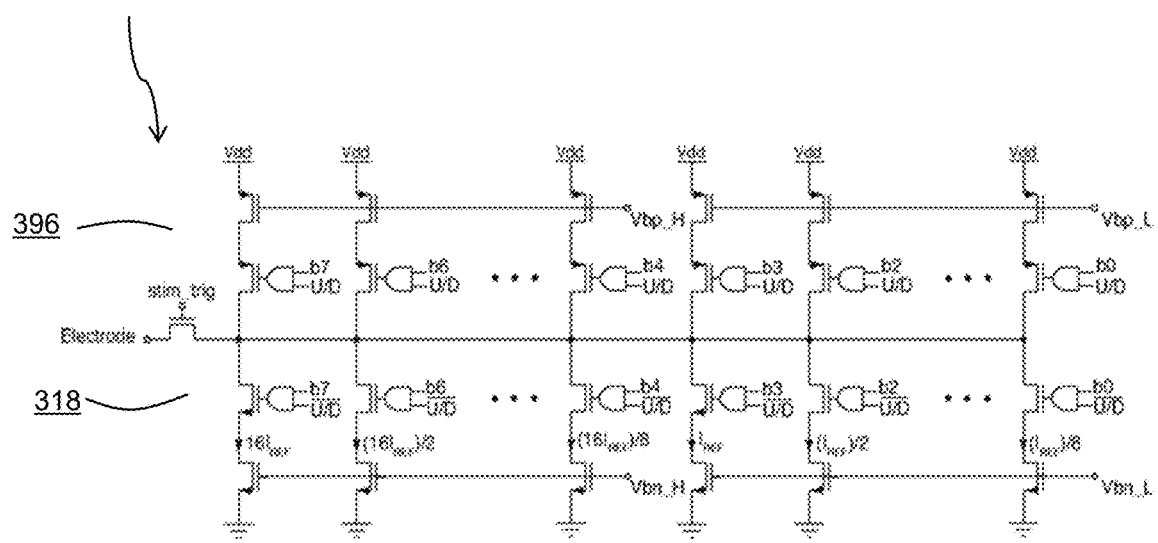
FIG. 14 shows a stimulator circuit for the die.

Referring now to FIG. 14, shown therein is an illustrative circuit schematic of an 8-bit arbitrary current-mode stimulator 304 of the die, providing closed loop neurostimulation. The current-mode stimulator 304 thus provides an embodiment of the IMDAC 339 of FIGS. 10, 13, and 352 of FIG. 11 As described above, once signal processing has been completed (either using on-chip signal processing unit 111, or through an off-chip computer that is placed in wired or wireless communication with the die), a decision may be made to stimulate a feedback signal to an area of the neurophysiological system according to a spatio-temporal stimulation profile. The decision may trigger a stimulation pulse-train 396. Once triggered, the stimulated feedback could be an electrical, optical, chemical or temperature change in the neurophysiological system in proximity to each stimulator electrode 318. The die may be designed to deliver stimulation feedback at multiple locations by having a dedicated stimulator 318 for each channel 303. To provide a high degree of freedom, an arbitrary pulse-generator may be provided. The pulse generator of FIG. 14 may be used to provide charge-balanced current pulses to living tissue but could be configured to provide other mentioned signals. This stimulator benefits from eight ratioed CMOS charge pumps that can generate an arbitrary waveform with 8 bits of resolution. The disposition of specifically 8 CMOS charge pumps is illustrative.

Figure 15:
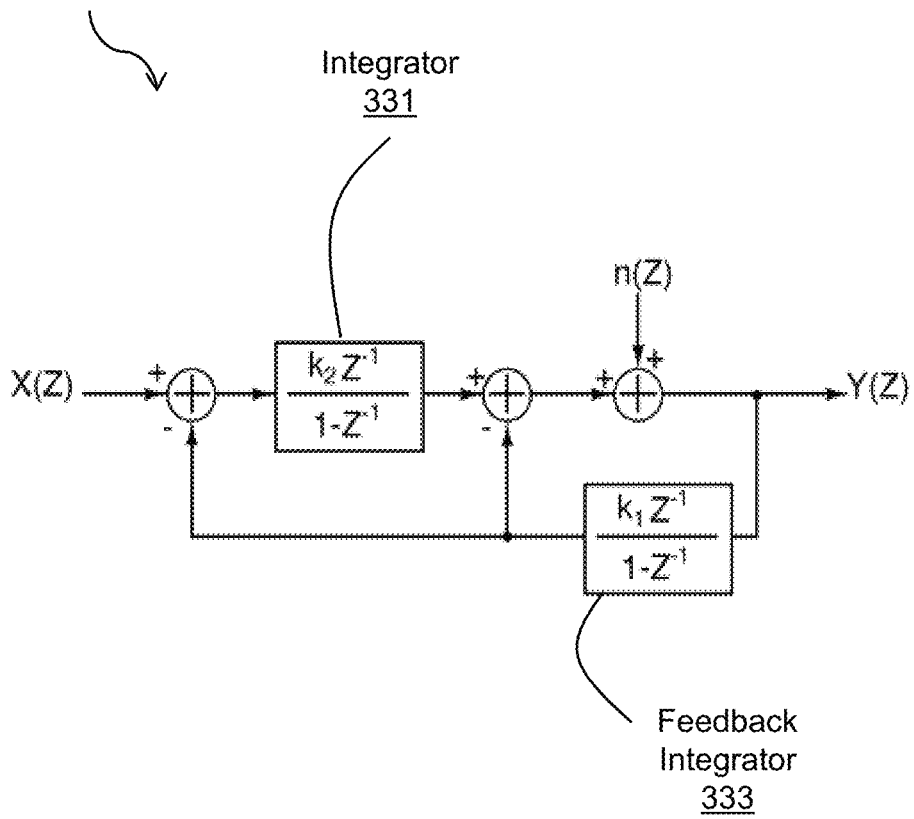
FIG. 15 shows an embodiment of the recording channels of the die wherein CMOS charge pumps of the stimulator circuit are utilized in the front end of recording channels.

Referring now to FIG. 15, in some embodiments, each one of the CMOS charge pumps used in the body of the arbitrary waveform generator may also be used as a charge pump in an embodiment 398 of each recording channel's front-end architecture. This allows the re-use of the stimulator circuit in the front-end architecture to provide an in-channel multiplier. FIG. 15 shows an embodiment of the block diagram of the front-end of the recording channels modified to replace the simple charge-pump with the 8-bit arbitrary waveform generator, wherein the feedback integrator 333 has a coefficient "$k_1$", and the integrator 331 has a coefficient "k2". This coefficient can be set with 8-bit accuracy.

For the multi-channel front-end 398 of FIG. 15, the system transfer function can be stated as follows:

$$\left(X(Z) - Y(Z)\frac{k_1 Z^{-1}}{1-Z^{-1}}\right)\frac{k_2 Z^{-1}}{1-Z^{-1}} - Y(Z)\frac{k_1 Z^{-1}}{1-Z^{-1}} = Y(Z) \quad (1)$$

$$H(Z) = \frac{Y(Z)}{X(Z)} = \frac{k_2 Z^{-1}(1-Z^{-1})}{(k_1 k_2 - k_1 + 1)Z^{-2} + (k_1 - 2)Z^{-1} + 1} \quad (2)$$

where, X is the input, Y is the output, k1 is the feedback integrator (Σ2 in FIG. 9(*b*) gain, k2 is the forward path integrator (Σ1 in FIG. 9(*b*)) gain, and the function is written in the z domain where z is the variable.

For the frequency range of 0–$f_0$ and for $f_0$, $$Z = e^{ST} = e^{j\omega T} = e^{j 2\pi \frac{f_0}{2 \cdot OSR} T_s} = e^{\frac{j2\pi}{OSR}} \quad (3)$$

Here we move from z domain to s domain so the variable becomes s. $f_s$ is the modulator sampling frequency, OSR is the oversampling ratio, and $f_0$ is the input signal bandwidth. With OSR>>1, |Z| can be approximated with:

$$\cos\left(\frac{2\pi}{OSR}\right) + j\sin\left(\frac{2\pi}{OSR}\right) = 1 + \frac{2\pi}{OSR} \quad (4)$$

Rewriting the transfer function, provides, $$H(Z) = \quad (5)$$

$$\frac{k_2(Z-1)}{(Z-1)^2 + k_1(Z-1) + k_1 k_2} = \frac{k_2\left(j\frac{\pi}{OSR}\right)}{\left(j\frac{\pi}{OSR}\right)^2 + k_1\frac{\pi}{OSR} + k_1 k_2} = \frac{j\pi}{k_1 \cdot OSR}$$

The final transfer function of Equation 5 illustrates that recorded signals are multiplied by the ratio of $1/k_1$ which validates the re-use of the current stimulator circuit for the front-end 398—each channel has a shift register cell to save its own multiplying coefficient. Further, the above equations demonstrate the flexibility of the system for different input signal amplitudes. The above equations show that if larger amplitudes (e.g. >100 mV) are to be recorded, then the OSR and $k_1$ can be set to larger numbers. In other words, $k_1$ and OSR set the system's gain and realize a variable gain front-end, hence realizing a very large dynamic range. Using this fact, the system is capable of recording a wide-range of amplitudes starting from 10 μV up to supply voltage which may be 1.2 V. This makes the system suitable for EEG, EMG, ECG and any other neurophysiological signal within that range of amplitudes.

Figure 16:
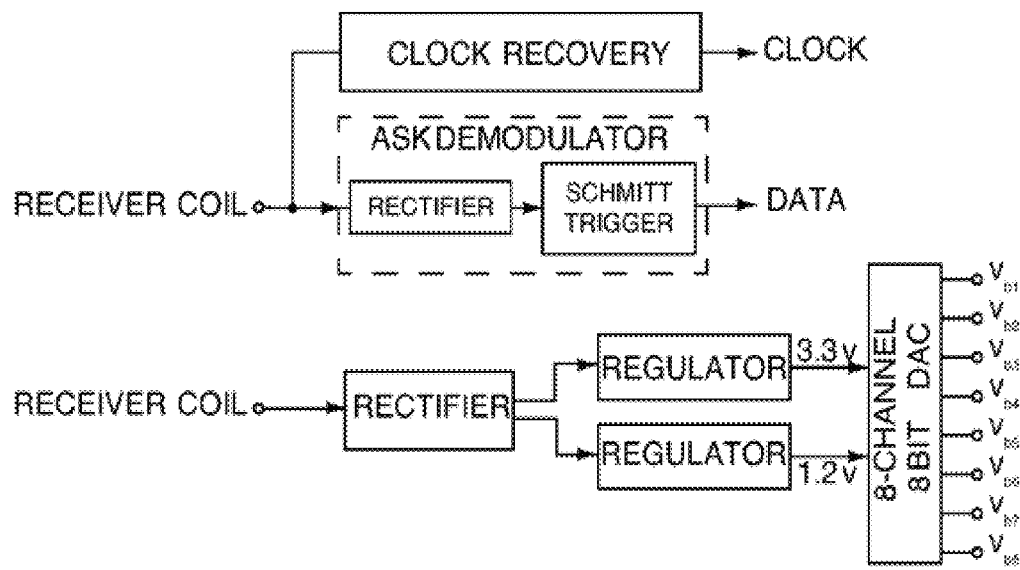
FIG. 16 shows a block diagram of a power management circuit that generates supply voltages from the energy received by power coil, as well as a data receiver that receives and decodes configuration commands from the wireless link.

Referring now to FIG. 16, shown therein is a block diagram of a possible circuit for the power coil 116. Specifically, FIG. 16 illustrates a power management circuit that generates supply voltages from the energy received by a power coil, as well as a data receiver that receives and decodes configuration commands from a wireless link. As shown, the power for the microsystem could be provided through a wired or a wireless link. If provided through wireless link, the die may thus comprise a power coil. As described above, power coil 116 may comprise power management blocks for receiving, rectifying and regulating separate power supplies for different blocks. FIG. 10 shows the block diagram of the power management system as well as an ASK data receiver that uses the same wireless link to receive configuration commands.

Figure 17:
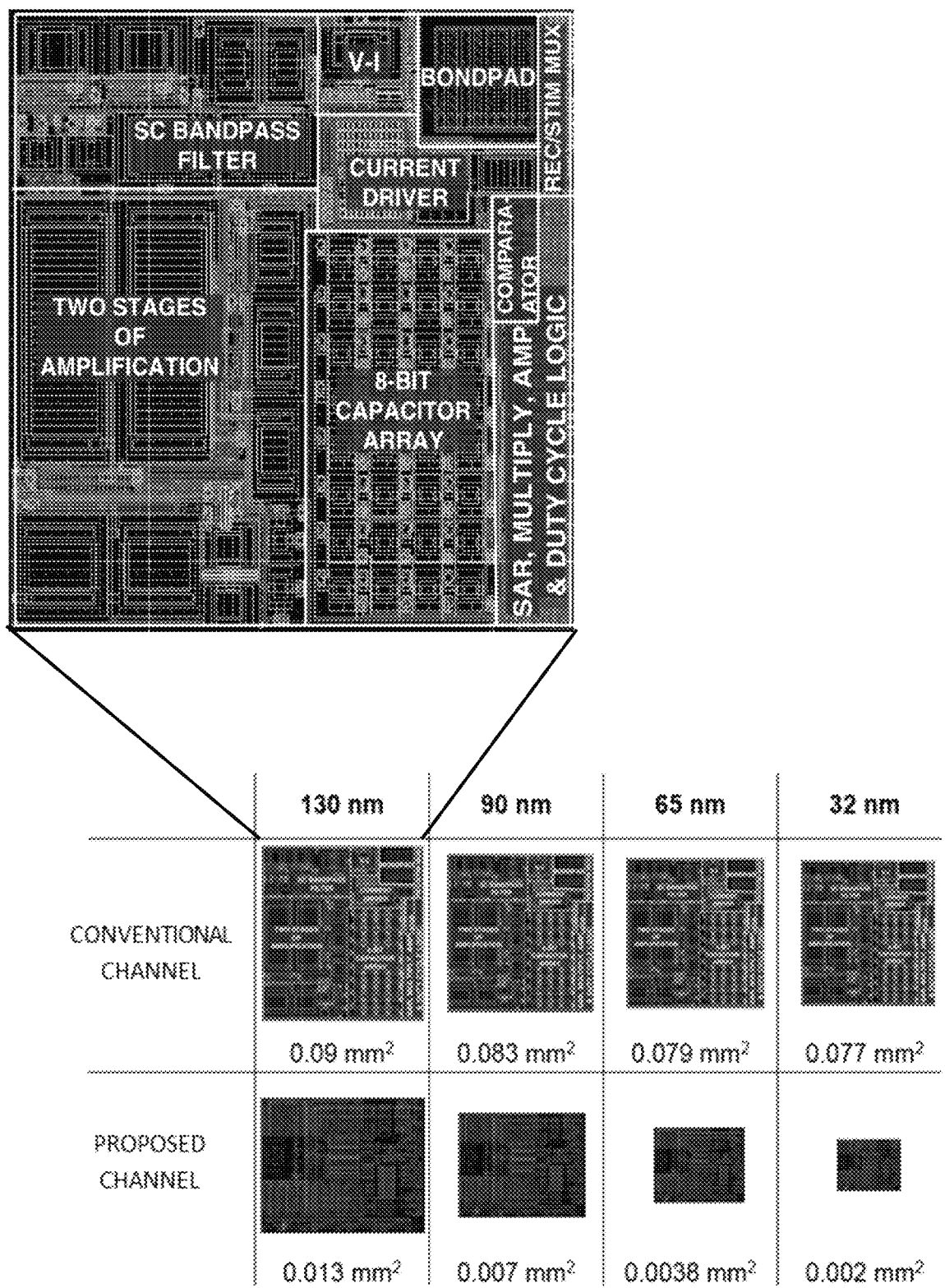
FIG. 17 shows possible area scalability of the die with the $\Delta^2\Sigma$-based design compared to the scalability of a die comprising a traditional AC-coupled recording channel components.

A benefit of the described Δ²Σ-based recording channels is its scalability. Due to the architecture used in the channel design, more than 90% of recording channels' area comprises active components which can scale down if the die is made in a newer technology. To illustrate this point FIG. 17 shows a possible scalability of the described embodiments compared to the scalability of a die comprising a traditional recording channel components when manufactured with incrementally newer technology nodes. As shown, while the conventional channel only scales down by 85% once it's take to 32 nm technology, the design according to the described embodiments may shrink to 15% of its current size in 32 nm CMOS technology. It should also be noted that the current design in the current technology may be as much as ~11× smaller than the conventional design thanks to removing input decoupling capacitors and using a delta-sigma ADC. This may provide the smallest neural recording channel compared to all other channels reported in the literature with same level of complexity.

Further embodiments of the recording channels will now be described which may provide for further minimization of the area and power consumption of the die.

Based on the embodiments of the die 106 described above, and the associated operational values for the components therein, in the context of ion amperometry (such as K+ or NA+ amperometry) and where the die operates in current recording mode, an approximately thousand channel implant die 106 may have approximately 0.08 μW power budget per channel 134 for use with recording, analog-to-digital-conversion and digital bandpass-filtering—which come up to approximately 100 uW in total power consumption for the die when including the power required for clock and bus generation and distribution circuits and data telemetry. The embodiments described below may help meet some performance requirements by minimizing size and power consumption of each channel by merging circuit blocks and simplifying the resulting schematic based on the known properties of the expected recording channel input signal.

Figure 18:
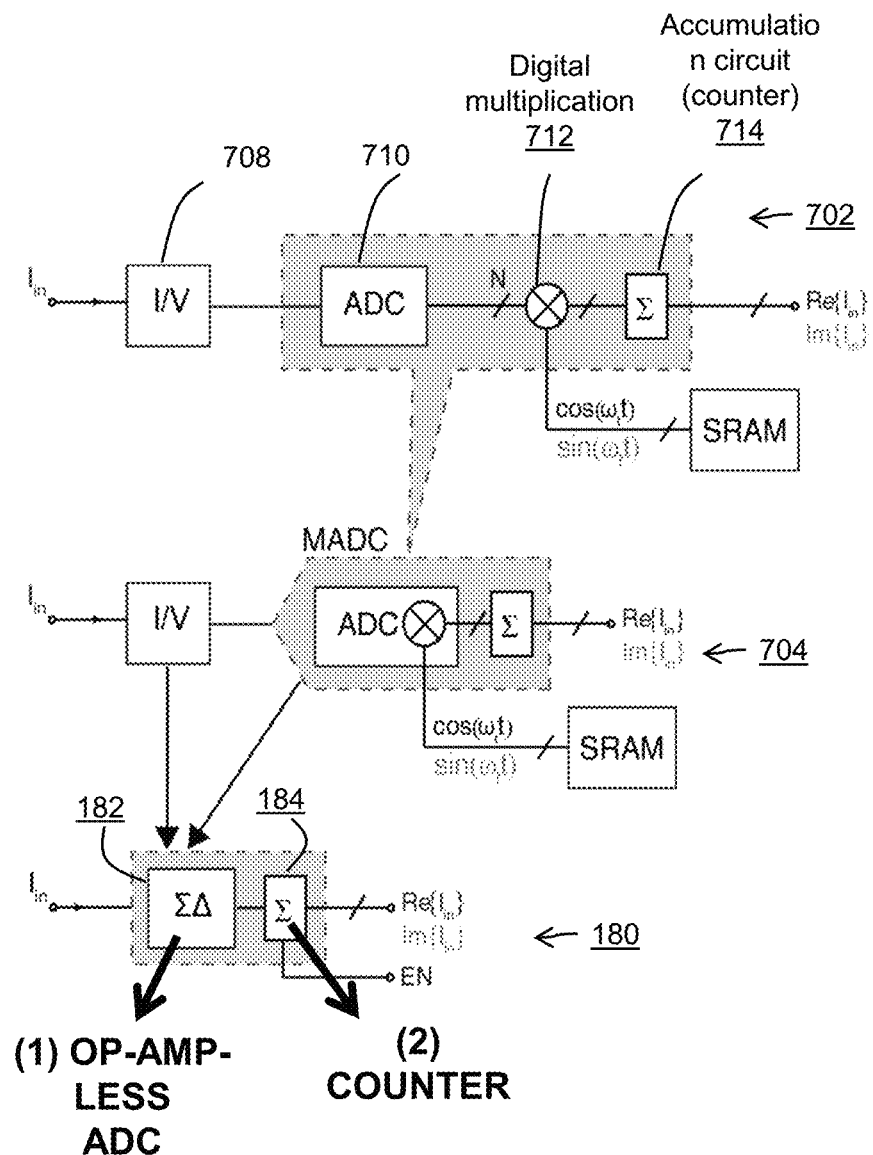
FIG. 18 shows circuit diagrams of an electrical current recording channel minimized in size and power consumption by merging circuit blocks.

Referring to FIG. 18, shown therein are recording channel block diagrams.

Embodiment 702 illustrates a conventional block diagram of an amperometric channel comprising a transimpedance amplifier 708 ("TIA") (current "I" to voltage "V" converter), an ADC 710, a digital multiplication 712 and an accumulation circuit (counter) 714. Depending on the digital coefficient used, the output of the counter will represent the real or imaginary part of the input current with respect to the applied voltage signal at the reference. Based on known values, a straightforward conventional block-by-block implementation of the transimpedance amplifier, ADC, and digital bandpass filter will not meet the low-power, high-sensitivity, and small-size requirements of the in vivo K+ imaging system proposed here. Embodiment 704 illustrates the block diagram of a simplified channel 134 where the size and power consumption have been reduced by performing a coefficient multiplication operation during the ADC operation in the mixed-signal domain. The channel diagrammed at element 180 provides a further minimization of the recording channel using a delta-sigma front-end ADC 182, as in some of the above-described embodiments of the multi-channel recording front end 302, which may significantly reduce size and power consumption.

Figure 19:
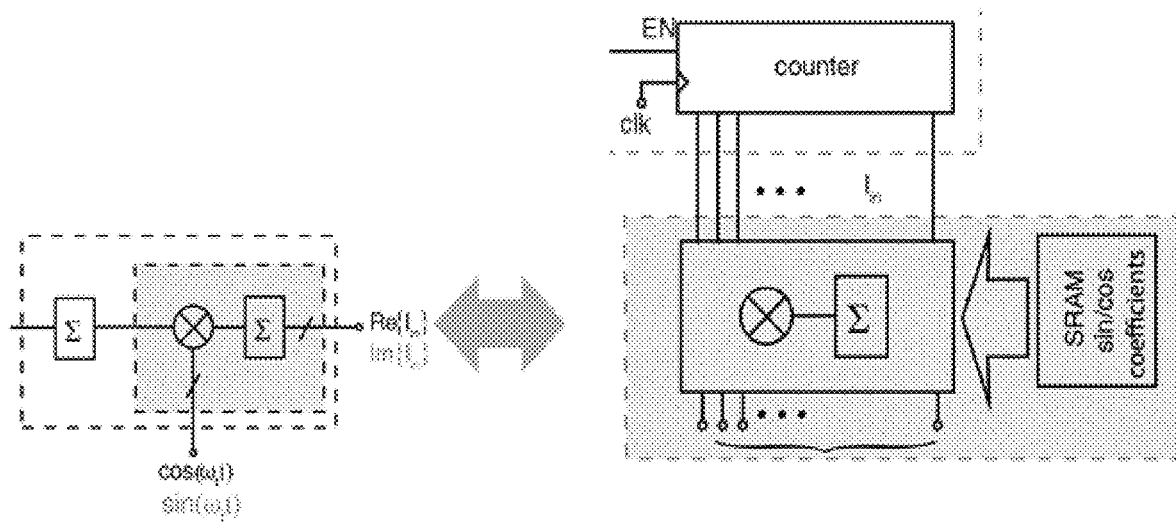
FIG. 19 shows an implementation of a digital multiplication operation performed on the output of a delta sigma ADC of a recording channel of the die after a decimation filter.
Figure 20:
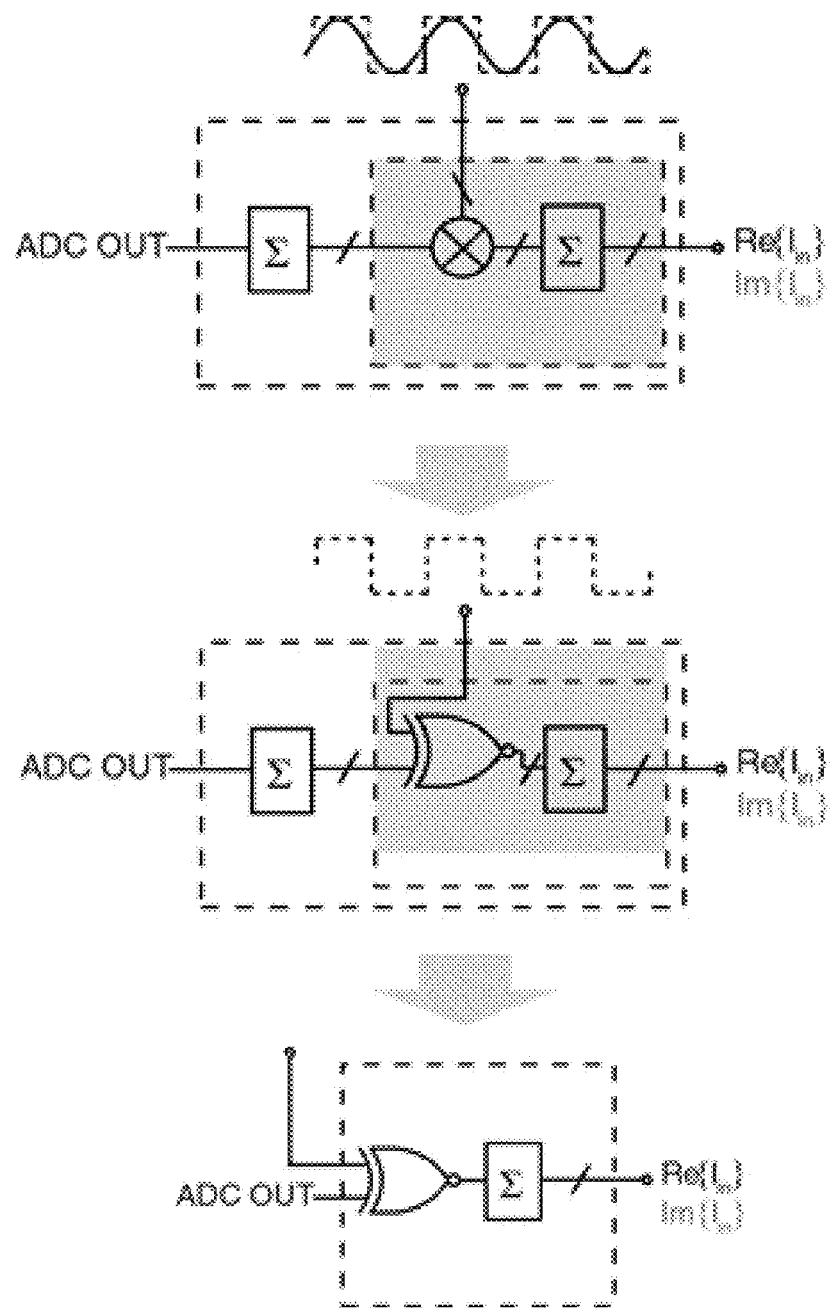
FIG. 20 shows the replacement of the 16-bit coefficient multiplication of FIG. 19 by a 1-bit XOR.

Referring now to FIG. 19 to FIG. 20, shown therein are embodiments wherein minimization of the size and power requirements of the circuit components may be achieved by approximating the multiplication coefficients by a single bit approximation of those values at block 184 of channel embodiment 180. The described channels provide embodiments of the die 106 wherein instead of multiplying recording channel outputs by high-resolution $\sin(\omega_o t)$ and $\cos(\omega_o t)$ waveforms, the described circuit only multiplies outputs by a 1-bit waveform ("1" when $\sin(\omega_o t)/\cos(\omega_o t)>1$ and "0" when $\sin(\omega_o t)/\cos(\omega_o t)<0$). A single XOR gate replaces the many digital logic gates of conventional IS circuits. As will be described below, in particular circumstances, this approximation may not significantly impact the outcome of recording due to the particular frequency spectrum of the input signal.

FIG. 19 shows a conventional implementation of a digital multiplication operation performed on the output of a delta sigma ADC after a decimation filter, i.e. particularly a conventional implementation of the sine and cosine waveform multiplication at ADC output. The digital coefficients are stored in memory and applied in a multibit MAC operation which requires SRAM storage, routing of a parallel bus of sin/cos coefficients to each recording channel, and implementation of a complete 16-bit MAC operation inside each channel.

FIG. 20 illustrates the replacement of the 16-bit coefficient multiplication by a 1-bit XOR according to block 184 of embodiment 180. By approximating the sinewave (and cosine waveforms) by a squarewave of the same frequency and phase, the multi-bit multiplication of the output of the first counter may be minimized by being replaced by a multi-bit XOR operation between the squarewave and the digital word at the output of the first counter. As the output of the first counter is reset periodically (to represent a low-pass filter), the first counter is eliminated by moving the XOR operation to the front and merging the two counters (the reset and the non-reset counters). Therefore the 16-bit digital coefficient multiplication and accumulation is replaced by a 1-bit XOR and a 1-bit counting operation.

Figure 21:
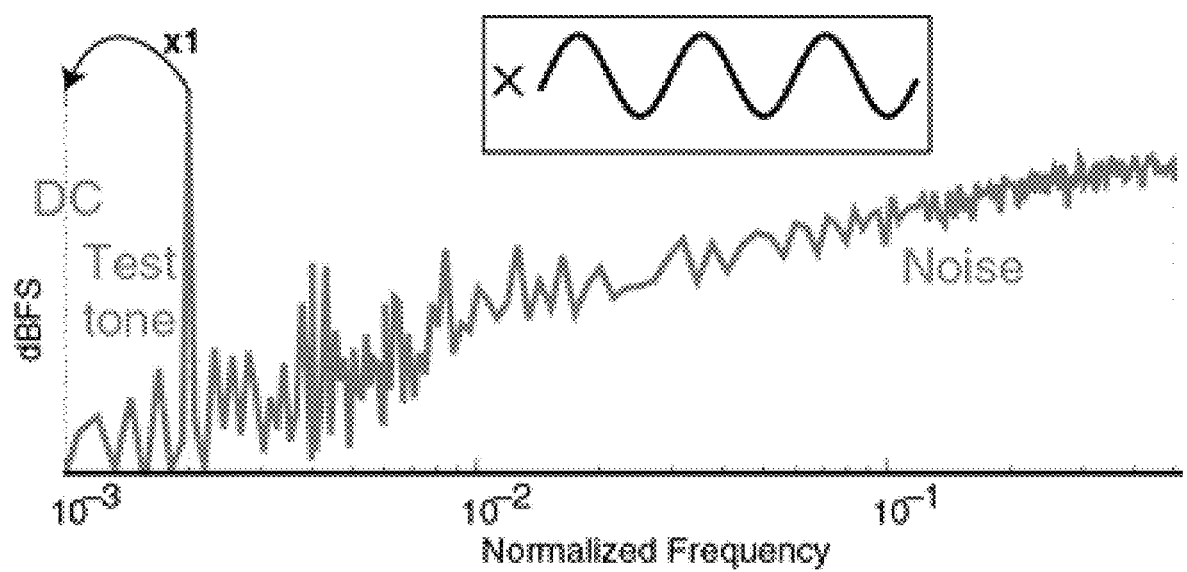
FIG. 21 illustrates decibels relative to full scale ("dBFS") against frequency for a tone signal after down-conversion by an ideal sine wave signal.
Figure 22:
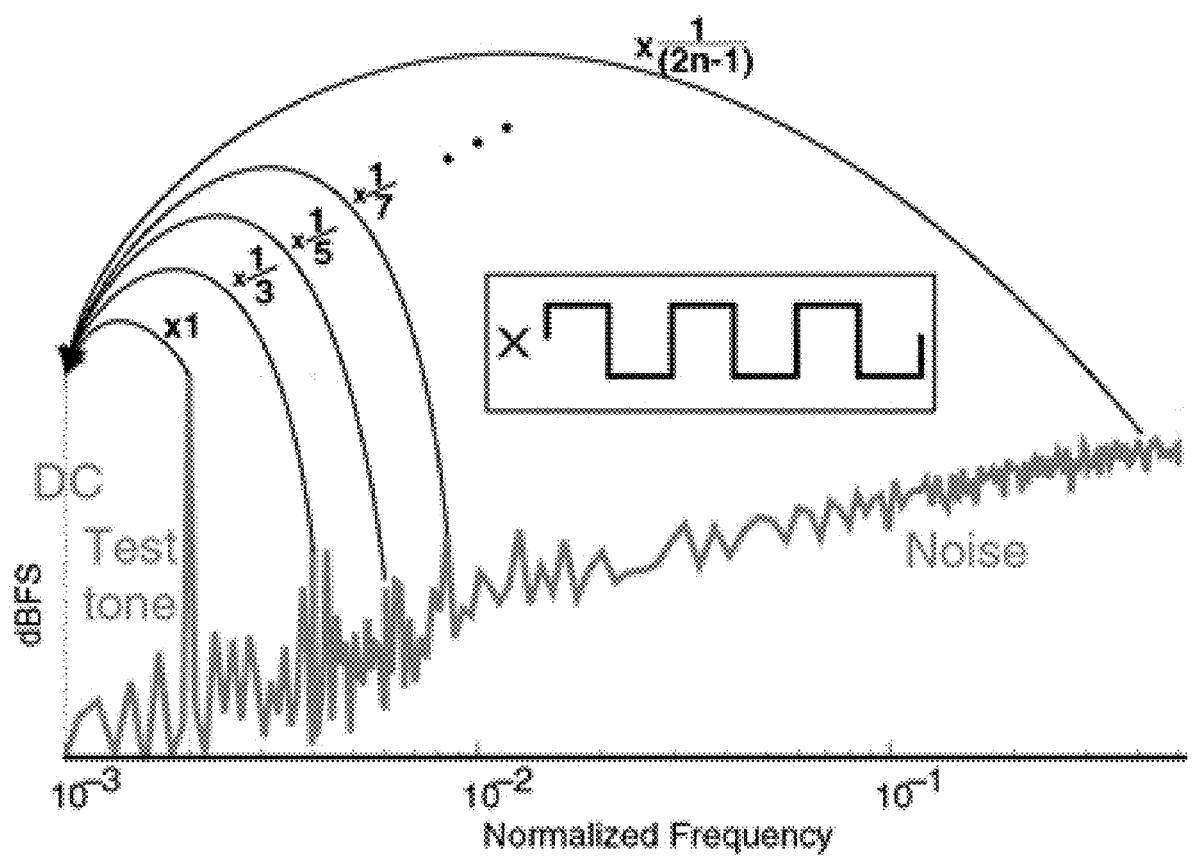
FIG. 22 illustrates dBFS against frequency for a tone signal after down-conversion by a squarewave approximation of a sinewave signal.

FIGS. 21 and 22 illustrate possible representations of decibels relative to full scale ("dBFS") against frequency for down-conversion of a signal by an ideal sine wave and a squarewave approximation, respectively. As shown in FIG. 21, multiplying the output of the sigma delta ADC by a high-resolution multibit-sinewave down-converts the target component of the ADC output spectrum to DC which is the value stored in the second counter. However, as shown in FIG. 22, the squarewave multiplication may also down-convert all the noise components occurring at the higher-order harmonics of the sinewave frequency. However, due to the noise-shaping property of the delta-sigma ADC, the down-conversion of the noise spectrum components may not corrupt the final output as the noise components folded down to DC by the first few harmonics may be minimal as compared to the signal component. As the noise components start to grow for higher harmonics, the weight of the higher order harmonics start to drop by a function of the same or more strength. Therefore, the noise shaping property of the delta-sigma ADC may effectively suppress the impact of the higher order harmonics of the squarewave during the proposed 1-bit multiplication.

Figure 11:
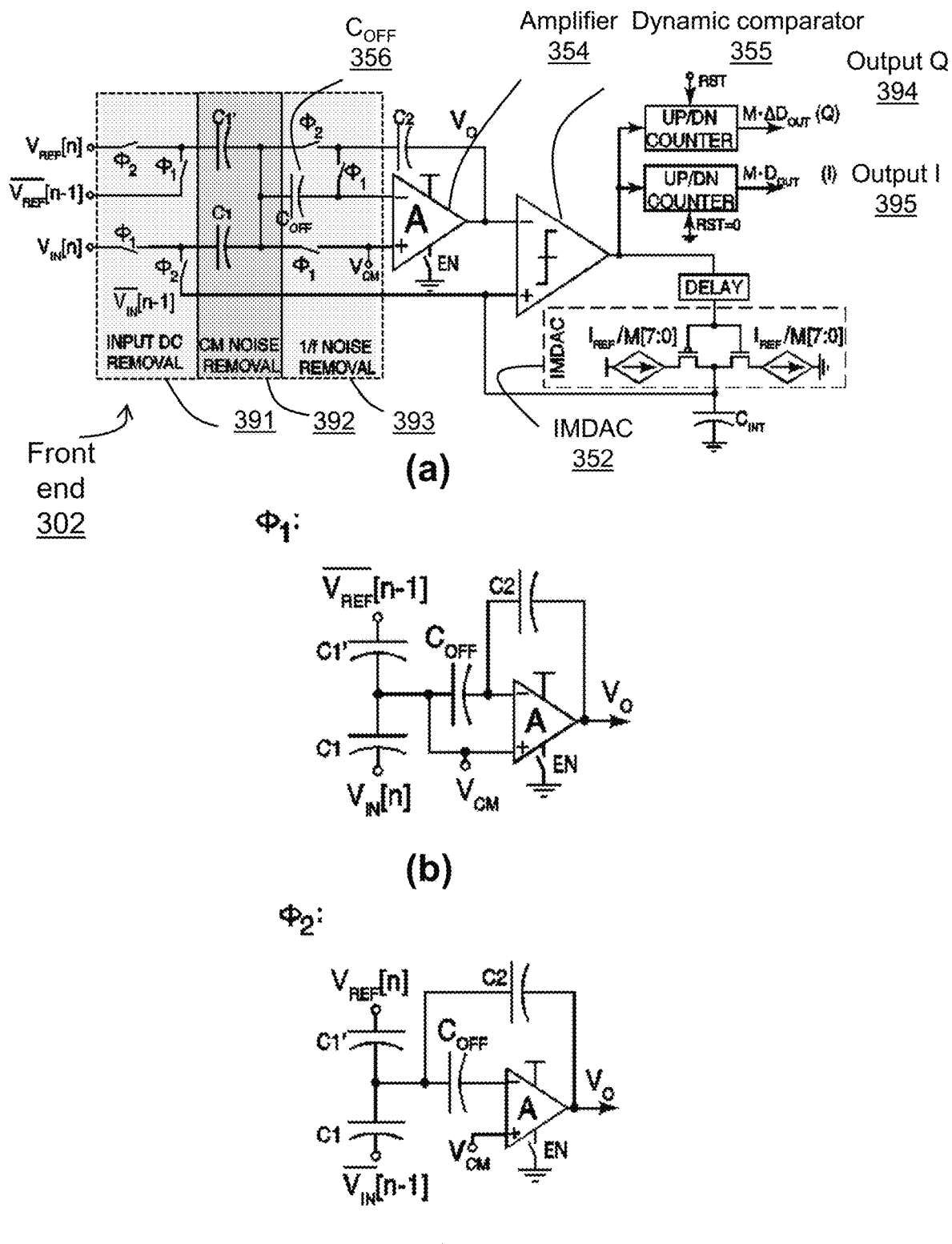
FIG. 11 shows circuit schematics of the $\Delta^2\Sigma$-based front end of recording channels of the die.
Figure 23:
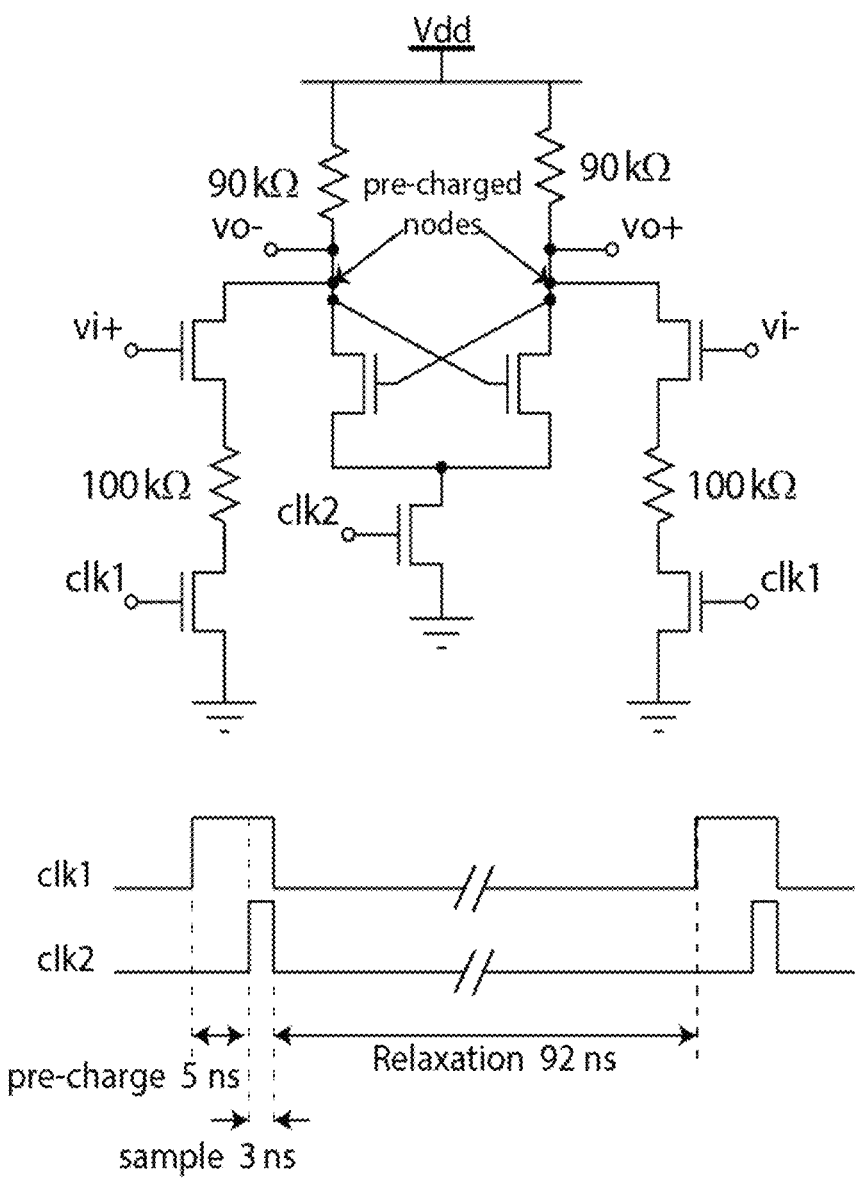
FIG. 23 shows a zero-kickback comparator circuit used to implement the delta-sigma ADC in the proposed recording channel.
Figure 24:
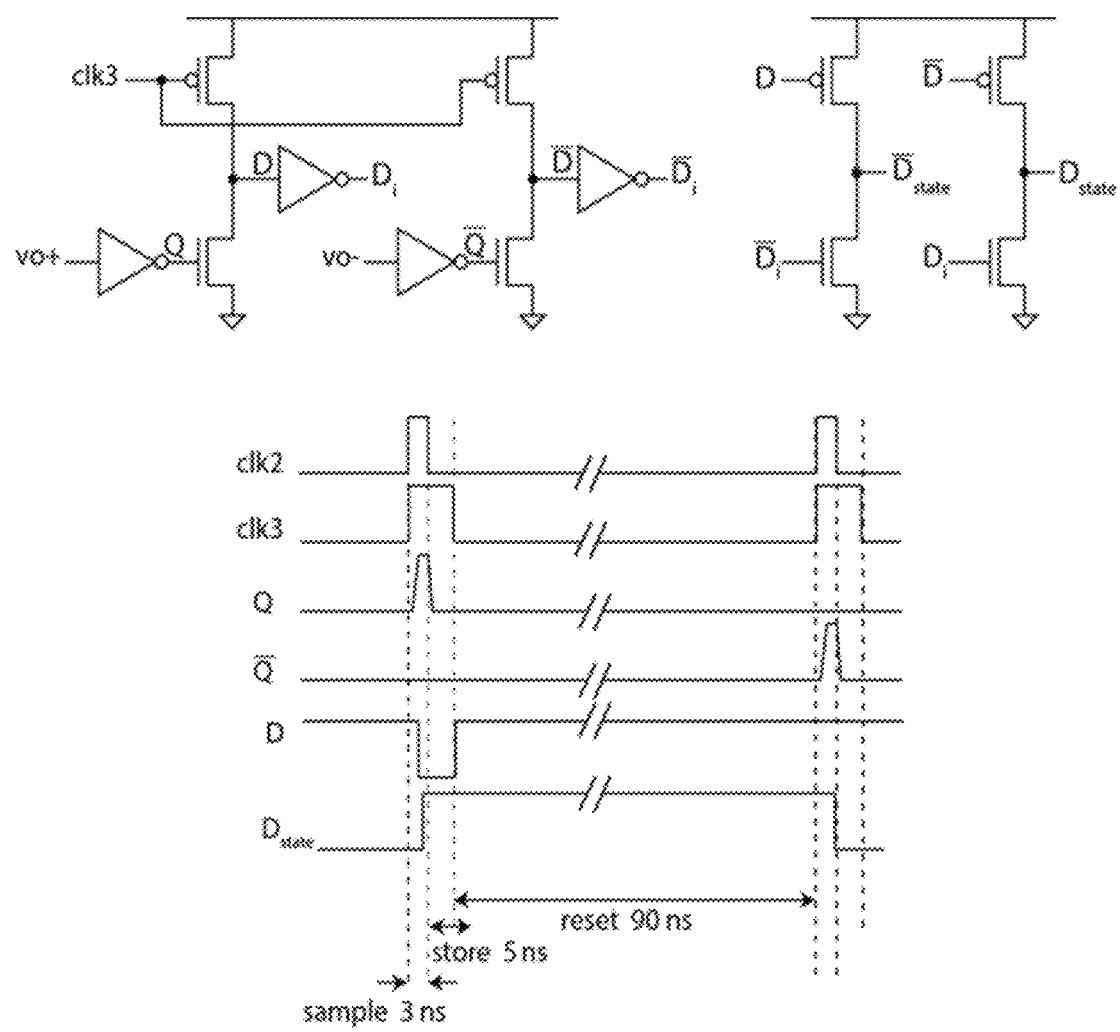
FIG. 24 shows dynamic logic buffers and other pulse shaping circuits necessary for connecting the comparator output to clocks.
Figure 25:
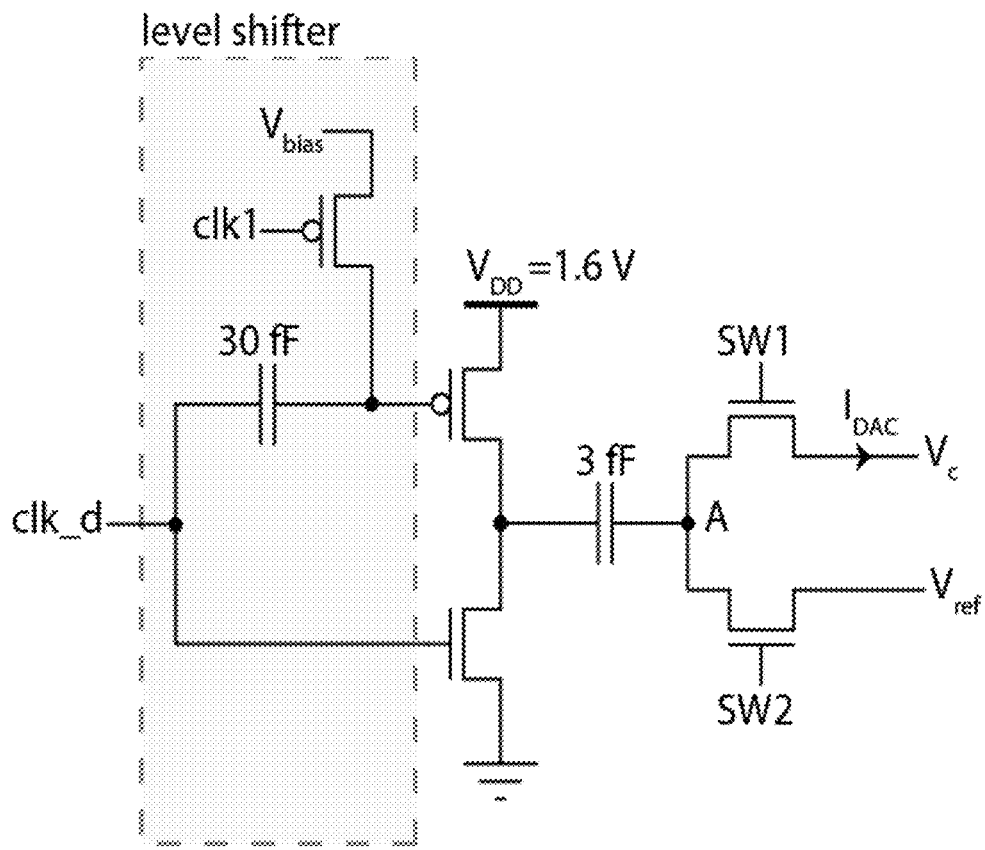
FIG. 25 shows a block diagram of the charge pump to implement the I-DAC in the feedback.

Referring now to FIG. 23 (illustrating a circuit schematic corresponding to block 355 in FIG. 11(*a*)), 24 (illustrating a circuit schematic corresponding to block "DELAY" in FIGS. 11(*a*)) and 25 (illustrating a low-power implementation of block 352 in FIG. 11(*a*) when the system is used in the current-recording mode), shown therein are transistor-level implementations of the different blocks of a delta-sigma ADC circuit provided in view of the embodiments described above. FIG. 23 illustrates a transistor-level schematic of a low power zero-hysteresis zero-kickback latched comparator circuit to implement the delta-sigma ADC for embodiments of the recording channel described above. The illustrated embodiment provides a zero-hysteresis comparator circuit which may reduce or eliminate signal distortion occurring due to removing the op-amp as compared to conventional implementations in embodiments of the recording channel. This circuit may reduce naturally occurring hysteresis in the comparator by isolating the output of the comparator from its input, which may minimize the impact of the previous comparator output on its current decision. FIG. 24 illustrates dynamic logic buffers and other pulse shaping circuits for connecting the comparator output to other clock, including the I-DAC in the feedback. FIG. 25 illustrates a block diagram of the ultra-low leakage charge pump to implement the I-DAC in the feedback.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A method for neurostimulation comprising:
applying a recording array to a subject;
recording, by the recording array, a plurality of neurophysiological signals corresponding to plurality of sites of the subject;
determining a phase synchrony among the neurophysiological signals;
associating selected phase synchrony calculations with the prediction or detection of a neurological or neurophysiological condition; and
delivering to the subject, by one or more stimulators, a stimulation in response to the predicted or detected condition,
wherein the stimulation comprises generating and applying an arbitrary current-mode waveform to a subset of the stimulators and wherein the arbitrary current-mode waveform is generated by a waveform generator that provides the neurophysiological signal and its derivative for use in the calculation of phase synchrony.

2. The method of claim 1, wherein the stimulators apply the stimulation comprising any one or more of an electrical charge, electrical current, electrical voltage, optical signal, chemical agent and temperature controlling signal.

3. The method of claim 1, wherein the recording array records signals by electroencephalogram, electrocardiograms, electromyography, or a combination thereof.

4. The method of claim 1, wherein the recording array is configured to record either current or voltage.

5. The method of claim 1, further comprising digitizing the neurophysiological signals prior to calculating the phase synchrony.

6. The method of claim 5, wherein the digitizing comprises applying an in-channel $\Delta\Sigma$ or $\Delta^2\Sigma$ neural analog-to-digital converter.

7. The method of claim 1, wherein the recording array comprises sixty four channels.

8. The method of claim 1, wherein the recorded signals are modulated by a 1-bit waveform, wherein the waveform is 1 when $\sin(\omega_o t)/\cos(\omega_o t) > 1$ and 0 when $\sin(\omega_o t)/\cos(\omega_o t) < 0$.

9. The method of claim 1, wherein the arbitrary current-mode waveform is generated by the waveform generator using a spatio-temporal profile determined specifically for the subject.

10. The method of claim 9, wherein the determination of the spatio-temporal profile comprises a one-sided simultaneous perturbation stochastic approximation (SPSA), wherein for any particular stimulation the one-sided SPSA applies exactly one sampling of the phase synchrony to compute a gradient approximation.

11. The method of claim 1, wherein the waveform generator provides an analog in-channel multiplier for the recording array.

* * * * *